(12) United States Patent
Saur-Brosch

(10) Patent No.: US 10,064,827 B2
(45) Date of Patent: Sep. 4, 2018

(54) METHOD FOR THE PRODUCTION OF A MOLDING

(71) Applicant: Roland Saur-Brosch, Heidelberg (DE)

(72) Inventor: Roland Saur-Brosch, Heidelberg (DE)

( * ) Notice: Subject to any disclaimer, the term of this patent is extended or adjusted under 35 U.S.C. 154(b) by 0 days.

(21) Appl. No.: 15/103,854

(22) PCT Filed: Dec. 11, 2014

(86) PCT No.: PCT/IB2014/003244
§ 371 (c)(1),
(2) Date: Jun. 11, 2016

(87) PCT Pub. No.: WO2016/009248
PCT Pub. Date: Jan. 21, 2016

(65) Prior Publication Data
US 2016/0324787 A1    Nov. 10, 2016

(30) Foreign Application Priority Data

Dec. 11, 2013  (DE) .................. 10 2013 113 891
Jan. 11, 2014  (DE) .................. 10 2014 100 269
Apr. 14, 2014  (DE) .................. 10 2014 105 325
Jun. 3, 2014   (DE) .................. 10 2014 107 820

(51) Int. Cl.
  *B30B 11/08*  (2006.01)
  *B30B 11/34*  (2006.01)
  (Continued)

(52) U.S. Cl.
  CPC .............. *A61K 9/2095* (2013.01); *A61J 3/10* (2013.01); *A61K 9/205* (2013.01); *A61K 9/2027* (2013.01); *A61K 9/2068* (2013.01); *A61K 9/2081* (2013.01); *B29C 43/006* (2013.01); *B29C 43/08* (2013.01); *B29C 43/146* (2013.01);
  (Continued)

(58) Field of Classification Search
  None
  See application file for complete search history.

(56) References Cited

U.S. PATENT DOCUMENTS 5,088,915 A * 2/1992 Korsch ............... B29C 43/003
                                                  264/109
5,256,046 A * 10/1993 Korsch ................. B30B 11/34
                                                  425/126.1
(Continued)

FOREIGN PATENT DOCUMENTS

EP    0349777 A1    1/1990
EP    0470679 A2    2/1992
(Continued)

OTHER PUBLICATIONS

Madhusudan Hariharan and Vishal K. Gupta, A Novel Compression Coated Tablet Dosage Form, Pharmaceutical Technology Year Book 2001, Oct. 1, 2001,pp. 14-19, Pharmaceutical Technology, USA.
(Continued)

*Primary Examiner* — Mary Lynn F Theisen

(57) ABSTRACT

The invention relates to a method for producing a molded piece (compression molding, molded body) using a compression molding device. The use of special construction features for the compression molding device, such as a spring-loaded punch, an intermediate punch and clamps, allows the advantageous production of molded pieces.

20 Claims, 26 Drawing Sheets

(51) Int. Cl.
*B29C 43/14* (2006.01)
*B29C 43/08* (2006.01)
*A61K 9/20* (2006.01)
*B29C 43/36* (2006.01)
*B29C 43/00* (2006.01)
*A61J 3/10* (2006.01)
*B29C 43/32* (2006.01)
*B29K 96/00* (2006.01)
*B29K 105/00* (2006.01)

(52) U.S. Cl.
CPC ............ *B29C 43/36* (2013.01); *B29C 43/361* (2013.01); *B30B 11/08* (2013.01); *B30B 11/34* (2013.01); *B29C 2043/147* (2013.01); *B29C 2043/3255* (2013.01); *B29C 2043/3621* (2013.01); *B29C 2043/3628* (2013.01); *B29C 2043/3665* (2013.01); *B29C 2043/3681* (2013.01); *B29K 2093/00* (2013.01); *B29K 2096/00* (2013.01); *B29K 2105/0035* (2013.01); *B29K 2105/251* (2013.01)

(56) References Cited

U.S. PATENT DOCUMENTS

| | | | | |
|---|---|---|---|---|
| 2003/0039691 | A1* | 2/2003 | Waterman | A61K 9/0004 424/471 |
| 2004/0247728 | A1* | 12/2004 | Ozeki | A61J 3/10 425/354 |
| 2005/0249811 | A1* | 11/2005 | Plachetka | A61K 9/1611 424/472 |
| 2007/0160670 | A1* | 7/2007 | Judy | A61K 9/2077 424/472 |
| 2008/0116606 | A1* | 5/2008 | Ozeki | B30B 11/34 264/255 |
| 2015/0021806 | A1* | 1/2015 | Mancini | B30B 11/027 264/113 |
| 2015/0328150 | A1* | 11/2015 | Maeda | A61J 3/10 424/465 |

FOREIGN PATENT DOCUMENTS

| | | |
|---|---|---|
| EP | 1158207 B1 | 7/2003 |
| EP | 1440790 A1 | 7/2004 |
| EP | 2165826 A2 | 3/2010 |
| EP | 1302304 B1 | 10/2011 |

OTHER PUBLICATIONS

Undisclosed author, Wie funktioniert eigentlich ein Kugelschreiber?, www.lehrerfreund.de/technik, Jul. 10, 2008, Lehrerfreund GmbH, Freiburg, Germany. Relevance is explained in the specification of the present application, p. 6, third paragraph (document explains how the push-push mechanism works).

* cited by examiner

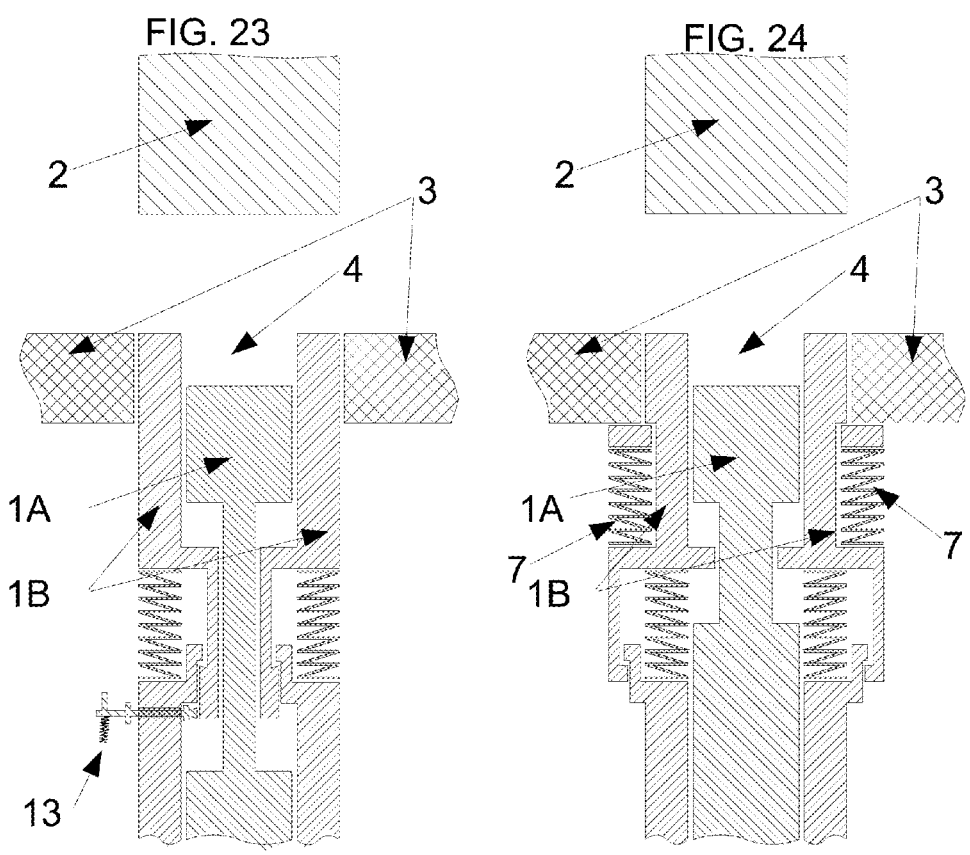

FIG. 27
FIG. 28
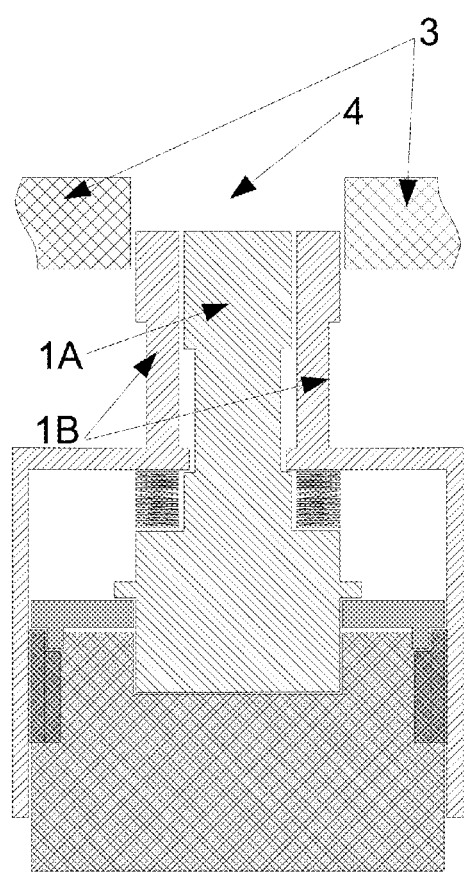
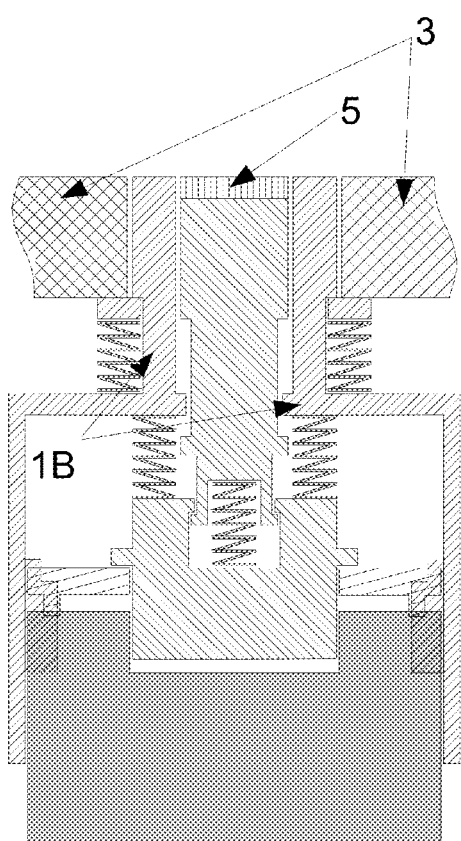

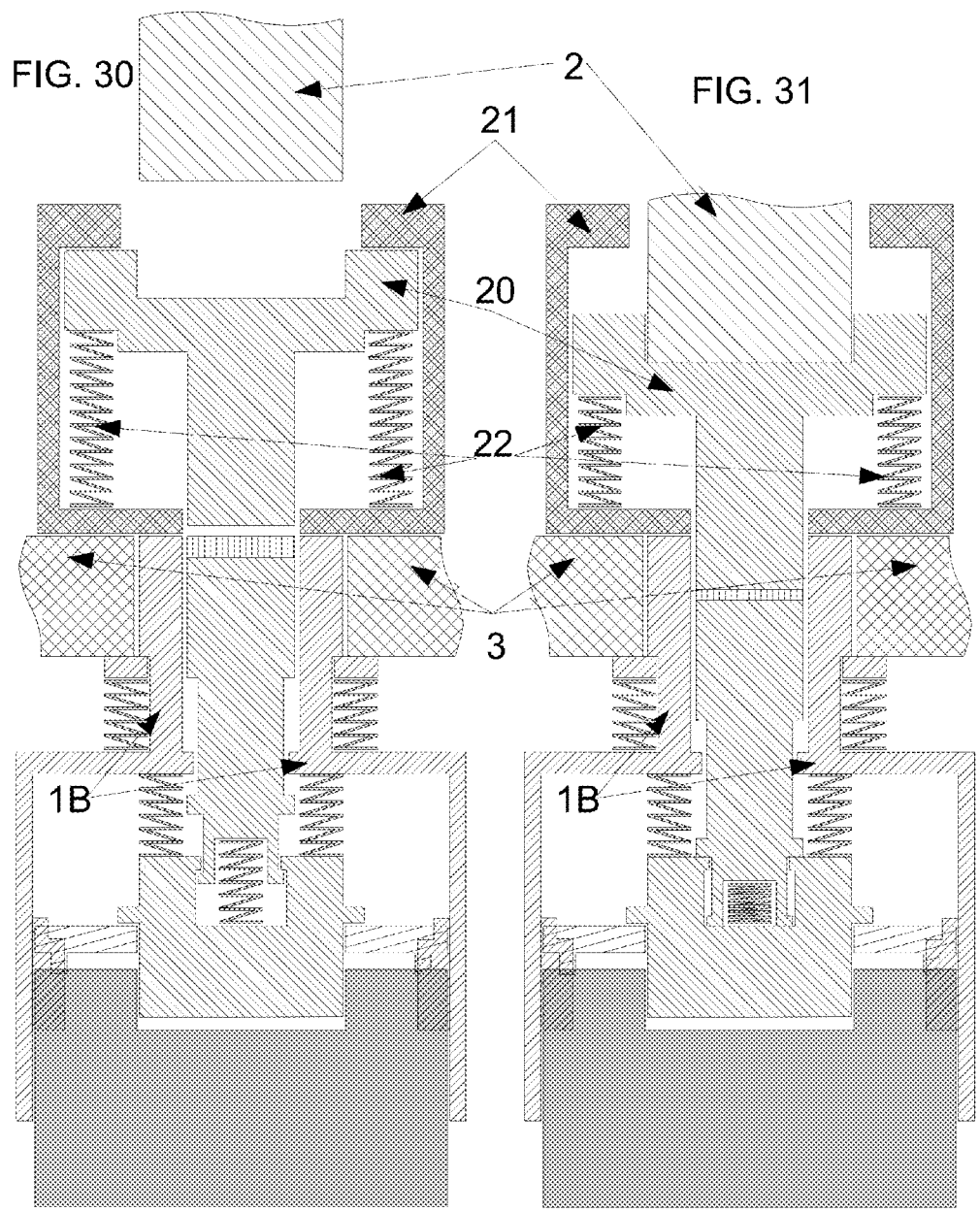

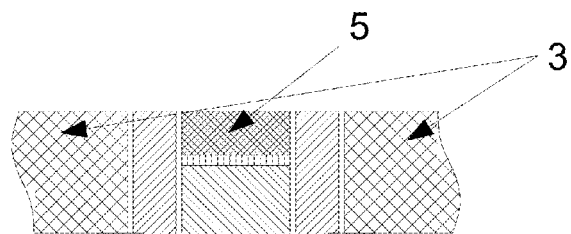
FIG. 32
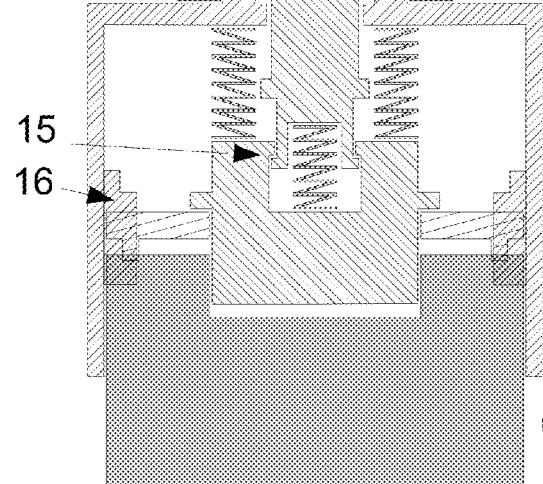
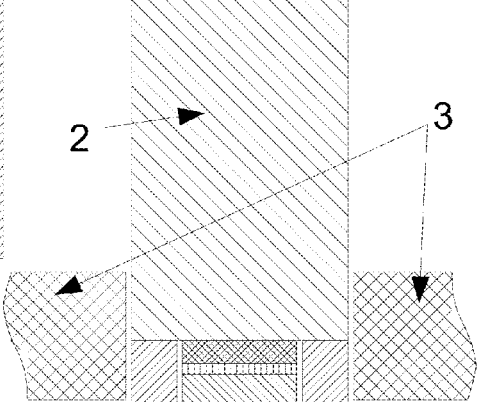
FIG. 33
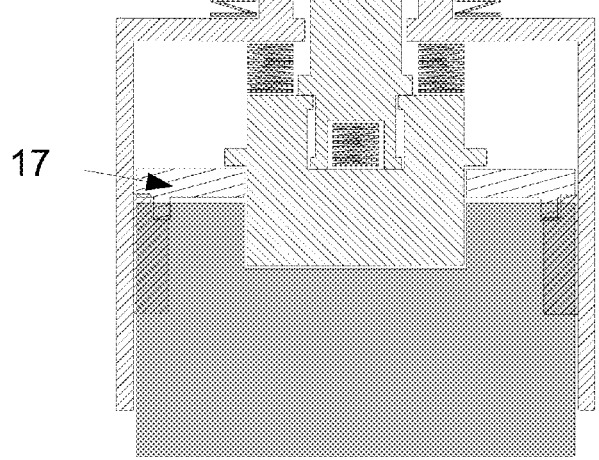

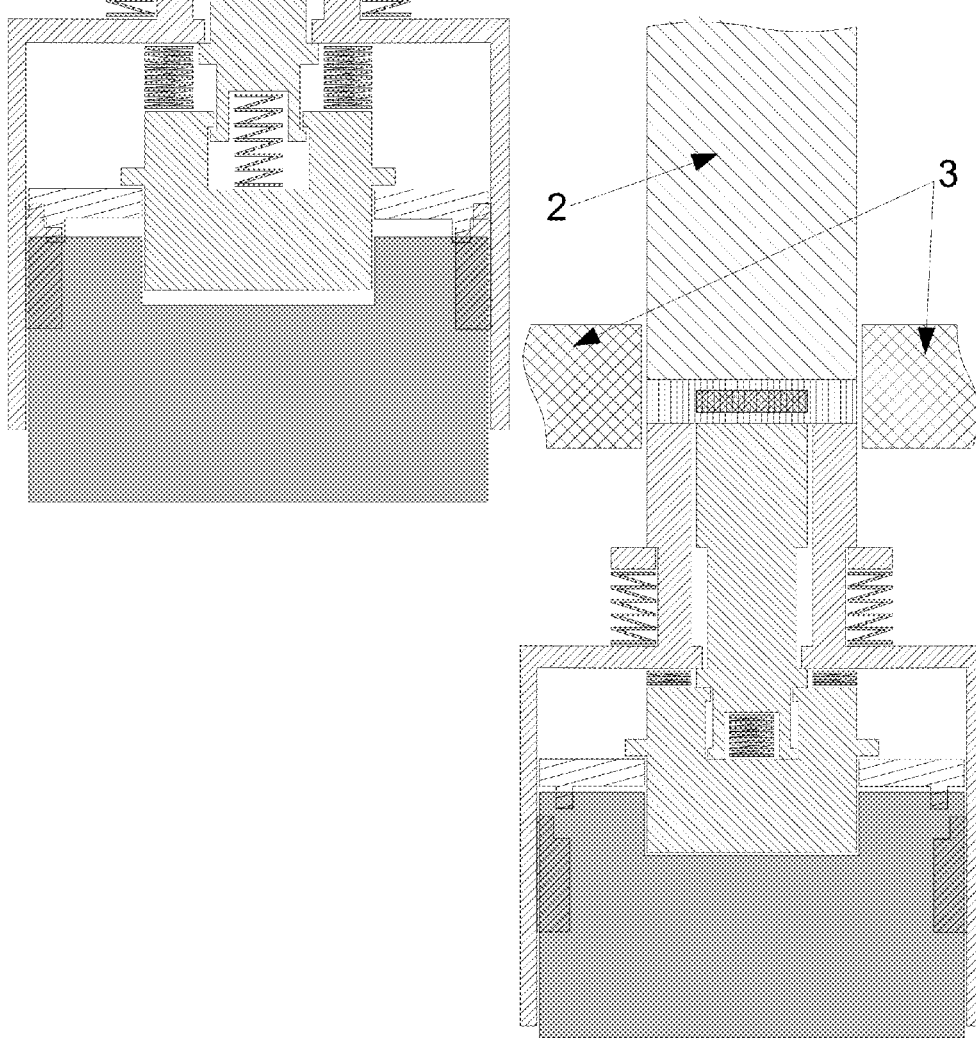

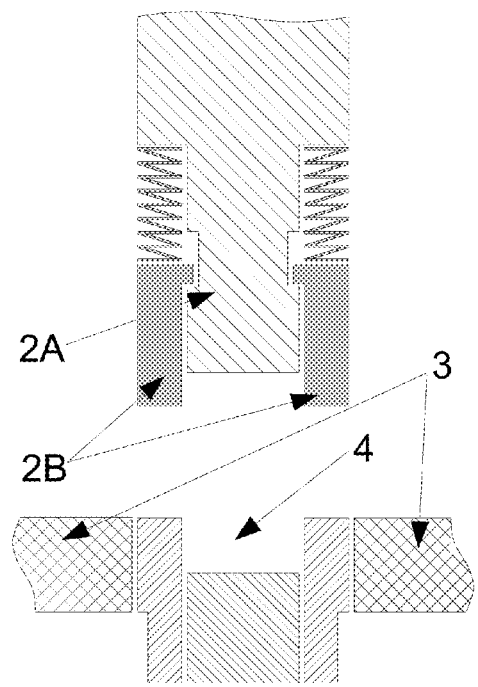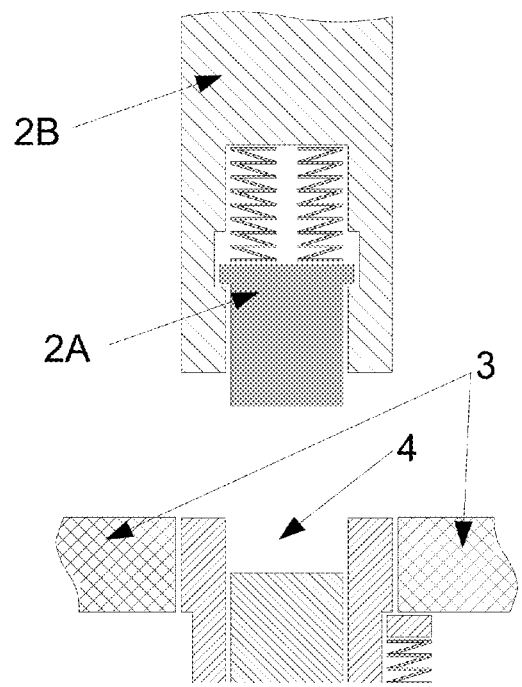

FIG.39
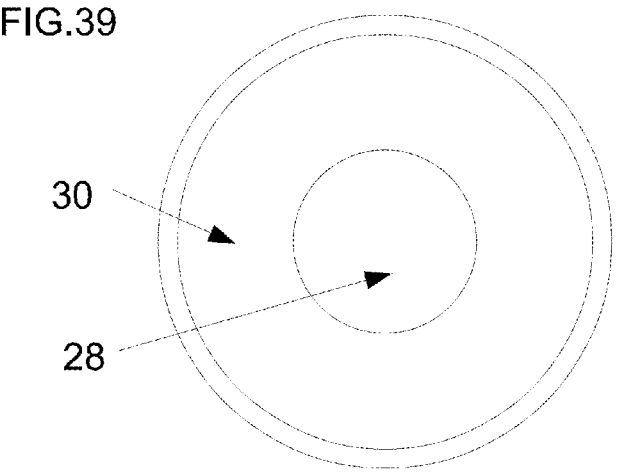
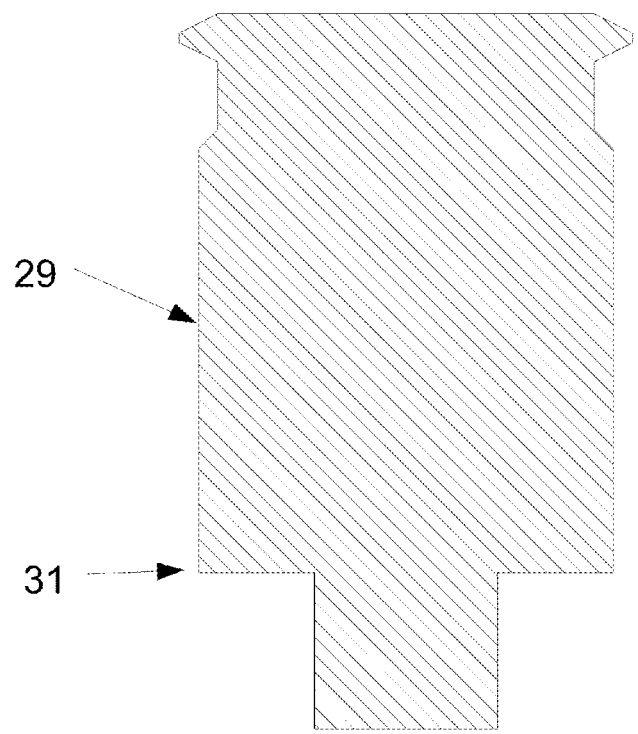

METHOD FOR THE PRODUCTION OF A MOLDING

The invention is a method for the production of a molding (compression molding, molded body) using a compression molding apparatus.

In the prior art it is known to produce moldings by the use of a compression molding apparatus. Examples of such moldings would include tablets for pharmaceutical or nutritional applications.

Typically, for this purpose, raw materials such as Powder, pellets or granules, optionally also mixtures thereof, are filled into molds (also referred to as dies) and pressed into the desired shape with the help of punches, through which pressure is applied on the raw materials.

An example of the production of such moldings is the compression of pharmaceutical active ingredients, optionally mixed or otherwise processed with excipients, into tablets. For this purpose, for example, a partial mold is provided which defines the outer lateral dimensions of the molding (die), and which, for example, consists of a horizontally arranged plate with one or more round, oval or otherwise shaped penetrations (holes, orifices).

The die or more of them may be fixed in another disk (die table). In some cases, the die table directly represents the die with its holes/orifices.

Furthermore, a lower punch is provided which defines the lower dimensions of the molding, and an upper punch is provided which defines the upper dimensions of the molding. These two punches, for example, consist of cylinders, which are formed with respect to the shape of the cylinder jacket in a way that they can protrude into and/or through the aforementioned penetrations with the least possible mechanical play.

If one lets the lower cylinder slightly protrude into the penetration, the lower cylinder and the plate with the penetration form of a kind of tub (filling space), into which the raw materials to be compressed can be filled. Then, the raw material can be compressed to the desired molding by the penetration of the upper punch into the penetration and the application of a downwards directed pressure on the upper punch, as well as the vertical fixation of the lower punch or an upwardly directed pressure on it.

Usually such methods consist of three kinds of process steps

1. Filling

The lower punch protrudes into the die from below, but only to the extent that its top edge remains below the top of the die by a certain measure.

The remaining space between the upper edge of the lower punch and the upper edge (filling space) of the die is filled with raw material.

This is usually done by providing a downwardly open container (filling shoe) in which the raw material is located which is moved across over the orifice (penetration) of the die (or the orifice is moved across under the filling shoe).

In the course of this raw material falls from the feed shoe into the remaining filling space.

The edge of the side wall of the filling shoe takes away all raw material above the upper edge of the die, so that the size of the filling space determines the amount of the raw material.

2. Pressing

The upper punch, which, where applicable, has previously been held ready above the die, is lowered, so that it protrudes into the die orifice of the die.

In doing so, the raw material is pressed against the lower punch (and also against the side walls of the die).

The lower punch may be slightly lowered before lowering the upper punch, so that the upper punch can slightly penetrate into the filling space and seal it upwardly without inadvertently displacing particles located on the surface to the side.

Thereafter, it is held in position or, if applicable, raised in order to assist in pressing.

The lowering of the upper punch and, if applicable, the raising of the lower punch determine the pressing force and the height of the molding.

After pressing, the upper punch is raised again, usually with its lower edge by more than the height of the molding over the upper edge of the die in order to enable the subsequent discharge step, or by more than the height of the filling shoe in order to enable another filling step.

Also, two pressing steps can be carried out instead of one, wherein the raw material usually is compressed at a lower compression force with the first pressing step and is then further compressed or plastically molded with the second pressing step at a stronger pressing force.

3. Ejection

The lower punch is raised, typically with its upper edge up to or above the upper edge of the die.

Thereby the molding is raised above the die and then usually extracted from the compression molding apparatus by a discharge apparatus or a deflector plate.

For producing multilayer moldings, steps 1 and 2 are carried out several times successively, preferably alternately.

In doing so, it may be advantageous to keep the pressing pressure of the initial pressing steps lower than that of the last pressing step.

Typically, such procedures are carried out using rotary presses.

The die table and the punches move around a common, usually vertical axis, the punches being brought into the positions for filling, compaction, plastic deformation and ejection with the help of rail-like cam tracks during the rotation. At the locations where a particularly severe raising or lowering of the punches is necessary (filling, compaction, ejection), these cam tracks are assisted by additional downpush pieces, pull-down tracks and lifting tracks. The die is filled via a rigidly arranged feeding device, the so-called filling shoe, which is connected to a storage container for the premix. The compaction pressure upon the premix is individually adjustable via the pressing paths for upper and lower punches, the pressure build up being done by rolling of the punch shaft heads past adjustable pressure rollers.

For the production of moldings which contain a core of a first raw material (core material), which is enveloped by a second material (shell material) (so-called core moldings), various methods are known:

One way to produce such a core molding is to insert a core into the filling space, which is smaller both in lateral and in vertical dimension than the filling space, prior to the second filling step.

Then is proceeded with the second filling step, by which the remaining filling space is filled up with raw material at the side of and above the inserted core.

In inserting the core a positioning as central as possible should be ensured, so that the thickness of the lateral filling with raw material is as evenly as possible.

Under some circumstances it is possible to dispense with the first pressing step prior to insertion of the core.

A disadvantage of this method is that an already prefabricated core must be provided and no powder, granules or other non-nuclear-like material can be used.

Furthermore, the as possible central placement of the core is difficult, especially when die (s) and punches are parts of a rotary press, in which centrifugal forces arise due to the rotation, which can decenter the core.

A method to produce a core molding which avoids both drawbacks is described in "A Novel Compression Coated Tablet Dosage Form", Madhusudan Hariharan and Vishal K. Gupta, Pharmaceutical Technology YEAR BOOK 2001.

There, an upper punch is described which consists of inner and outer punch which are displaceable vertically relative to each other (virtually a two-part coaxial punch).

Typically, the outer punch has a certain wall thickness which is uniform over the entire circumference and the inner punch fills the orifice of the outer punch with the lowest possible mechanical play.

At the first filling step the raw material for the envelope (shell material) is filled in.

At the first pressing step the inner punch is shifted downwards relative to the outer punch.

Upon penetration of the inner punch into the filling space, a part of the raw material must be displaced towards the lateral die walls so that side walls can be formed which are higher than the bottom layer (bottom plate) pressed below the inner punch and a kind of cup-shaped molding is formed.

For this purpose, it may be necessary to have the inner punch beveled into a blunt tip.

By the downwards displacement of the inner punch the outer punch penetrates into the die later and compresses the laterally displaced material into the side walls of the cup-shaped part.

Typically, the bevel of the inner punch continues at the outer punch, so that the side walls have a correspondingly inwardly sloping bevel on their upper edge.

After raising of the upper punch the filling step for the raw material of the core (core material) is carried out.

By further lowering of the upper punch with downwards displaced inner punch, the core material is pressed into the cup-shaped filling space now encompassed by the partial molding.

After raising of the upper punch the inclined inwardly sloping upper edge of the side walls ensures that core material left behind on it slips towards the inside onto the pre-pressed core.

If necessary, this material may be pressed onto the already pre-pressed core material once more by a further lowering of the upper punch with shifted downwards inner punch.

Thereafter, the third filling step is carried out. This is done with shell material.

At the last pressing step the inner punch and outer punch of the upper punch are no longer displaced vertically with respect to each other.

Thus the lower surface of the upper punch is a uniform surface that, if applicable, forms a blunt tip at a slight incline.

Upon lowering of the upper punch, the cover plate (cover layer) of the molding is formed and the entire molding is compressed to its final height.

A disadvantage of this method is that the upper punch must be slightly pointed in order to partially displace the material of the first filling towards the side walls and to bevel the side walls at the top so that core material remaining on it can slip inwardly.

Because of this, the shaping of the molding is restricted.

In addition, because of this no uniform thickness of the bottom plate is possible because with a bevel of the lower punch to the same extent as that of the upper punch the lateral displacement of the shell material with the first pressing step does not take place to a sufficient degree.

Furthermore, the raw material under the inner punch is compressed more severely than under the outer punch so that the properties of the bottom plate and the side walls differ (e.g. strength, dissolution behavior, density, etc.).

A further disadvantage is that, if applicable, two pressing steps are required for the core material.

Another disadvantage is that the inner and the outer punch of the upper punch must be guided separately, which requires a complicated management of the punches.

Another method to produce a core molding is disclosed in EP1302304B1.

There, both upper and lower punches are described as inner and outer punch.

These punches are constructed similarly to in "A Novel Compression-Coated Tablet Dosage Form", but not necessarily with the beveled tip.

For the first and second filling and pressing steps the outer punch of the lower punch is raised vertically so that it lines up as flush as possible with the top of the die.

Thereby a smaller lateral dimension in the filling space is created.

Likewise for the first and second filling and pressing steps the outer punch of the upper punch is raised vertically so that it does not enter the filling space during the lowering of the upper punch.

Thus a two-layer partial molding is produced, wherein the lower layer consists of shell material and the upper layer consists of core material.

Before the third filling step, the outer punch of the lower punch is lowered vertically so that it lines up as flush as possible with the inner punch.

Thereby, in the third filling step, which then takes place with shell material, both the filling space above, and the now freed space at the side of the partial molding is filled with shell material.

For the third pressing step the outer punch of the upper punch is lowered vertically so that it lines up as flush as possible with the inner punch.

Upon lowering of the upper punch, the cover (the cover plate) of the molding and the side walls are formed and the entire molding is compressed to its final height.

A disadvantage of this method is that two punches with inner and outer punch must be used, which must be guided separately, which requires a very complicated guiding of the punches. This can usually be realized only with very elaborately constructed presses. Furthermore thereby the maximum speed and therefore the production capacity per unit time become limited.

DESCRIPTION OF THE INVENTION

The invention provides an optimized method which is characterized by the elements of the claims. The invention also provides a punch which is suitable for the implementation of a preferred embodiment of the method.

By use of a lower punch (1) with which the outer punch (1B) can be shifted downwards via pressure from above it is possible to use an upper punch (2) which is one-piece or with which inner (2A) and outer punch (2B) cannot be shifted with respect to each other also with the first and second pressing step.

With lowering the upper punch the lower outer punch recedes downwards as soon as the upper punch exerts pressure on it. The upper punch can thereby compress raw materials (5) located in the filling space (4) without a two-part upper punch with retracted (raised) outer punch being required therefor.

Since with these steps the lower outer punch is not actively pulled downwards but passively follows the upper punch, no gaps occurring due to not absolutely synchronous movements can originate between the punches and the raw material cannot leak sidewards during the pressing step.

In a preferred embodiment the invention suggests that the upper punch has a slightly elevated surface the lateral dimensions of which correspond to the lower inner punch.

Thereby the sideward seal of the filling space can be improved. The step in the top side of the molding originating from this is usually tolerable.

In a preferred embodiment the invention suggests carrying out the upper punch two-part and lowering the upper inner punch (2A) slightly downwards with respect to the upper outer punch (2B) in order to achieve such an improvement of the seal of the filling space. The upper punch preferably is carried out so that the upper inner punch can be shifted upwards by pressure from below so far that it is flat with the outer punch again (e.g., mounted spring-loaded with limit stop, see upper punch in drawing 38). Thereby an improved seal of the filling space as well as a level surface of the molding can be achieved. In a preferred embodiment the downwards directed displacement of the inner punch amounts to maximum 20% of the desired height of the molding, more preferably maximum 10% and particularly preferably maximum 5%. The spring force preferably is chosen significantly lower than the pressing force of the first two pressing steps. Preferably it is less than 30% of the lesser of the two pressing forces (with renunciation of pressing step 1, however, as measured in pressing step 2), more preferably less than 10% and even more preferably less than or equal to 5%.

One way to realize the slidability of the lower outer punch by pressure from above is the spring-loaded mounting of the guide tracks (guide cams, lower punch tracks, Pull-down tracks etc.) that determine the position of the outer punch. In doing so, these guides can be mounted spring-loaded, for example, only where they raise the outer punch relative to the inner punch, so that where it has not been raised, for example with the last pressing step, a compression also of the side walls can be achieved.

However, in a further embodiment they may be mounted spring-loaded on their entire length. Then a support of the guide takes place with the last pressing step through additional pressure rolls.

In a further embodiment, the spring suspension is integrated into the outer punch (See drawings 15 to 18 members 6), so that a spring suspension of the guide tracks (punch guide/guide curves) can be dispensed with.

In another embodiment, the spring force is chosen such that it is greater than the pressure from above, to which the lower outer punch is exposed to with the last pressing step (pressing pressure per unit area of the molding times upper surface of the lower outer punch). This ensures that the outer punch which was lowered before the final filling step does not lower further with the last pressing step. Although with the preceding pressing steps the upper punch then must be moved downwards with a greater force.

Since with these pressing steps usually in any case a lower pressing pressure is needed upon the raw material, and the surface of the outer punch is usually less than 50% of the surface area of the molding, this force can be realized with conventional pressure appliance systems.

This embodiment with regard to the choice of the spring force is possible both in spring-loaded guide tracks as well as with a spring suspension integrated into the outer punch.

In a further embodiment with a spring suspension integrated into the outer punch the spring travel of the upper (spring-mounted) part of the outer punch with respect to the lower part of the outer punch is limited upwardly. This can be realized, for example, by a limited length in the pressure-free state of the spring or the springs used or by a corresponding limit stop (drawing 20, element 10).

This results in a more accurate alignment of the upper edge of the outer punch being possible, for example, to the upper edge of the die (useful, for example, with the first two filling steps) or to the upper edge of the inner punch (for example, with the last filling step).

In another embodiment, the spring travel of the outer punch (or with outer punches with integrated spring suspension, the spring travel of the upper part of the outer punch) is upwardly limited with respect to the die, for example, by a corresponding limit stop (see FIG. 22, item 9). This facilitates the alignment of the upper edge of the outer punch with the first two filling steps.

In another embodiment, with a spring suspension integrated in the outer punch the spring travel of the upper (spring-loaded) part of the outer punch is downwardly limited relative to the lower part of the outer punch. This can for example be realized by a finite compressibility of the spring or the springs used or by a corresponding limit stop (drawing 19 item 8).

Thereby, for example, the spring force of the spring-loaded mounting of the upper punch can be chosen smaller than with the embodiments with which the spring force is chosen such that it is greater than the pressure from above, to which the lower outer punch is exposed to at the last pressing step, in order to keep the position of the outer punch with the last pressing step.

For example, with an embodiment, with which the spring travel of the upper (sprung) part of the outer punch is downwardly limited relative to the lower part of the outer punch, after the last filling step the upper punch is first lowered to such an extent that sufficient pressure is applied upon the filled raw material from above, in order to be able to raise the lower part of the lower outer punch up to the limit stop (or the maximum compressibility of the spring), without the upper part rising significantly.

Thereafter, the upper punch can be charged with the full compression pressure and compress the raw material, without the upper part of the lower outer punch being able to recede downwards.

In a further embodiment of the invention the relocatability of the outer punch (or, with outer punches with integrated spring suspension, the spring travel of the upper part of the outer punch) with respect to the inner punch is limited downwardly. This can be realized, for example, by a limit stop (see drawings 21 and 22, element 11). Preferably, the position of the limit stop is adjustable with respect to its height. This can be done, for example, by insertion of shims or via screw adjustable limit stops.

Preferably the limit stop position is adjusted so, that with reaching the limit stop the upper edges of the inner punch and the outer punch where their edges are facing one another are at the identical height. Through this, e.g., by use of guide rails for the outer punch, these can be mounted spring-loaded everywhere without needing additional pressure rollers. The required pressing pressure is passed on by the inner punch via the limit stop to the outer punch.

So that with an embodiment with which the spring travel of the (upper part of the) outer punch relative to the die is limited upwardly by a limit stop, this limit stop does not interfere with the ejection step with which usually at least one of the lower punches is raised above the upper edge of the die, it is carried out spring-loaded in a further embodiment (see drawing 24, element 7). Preferably the spring used for this is stronger than the one which presses the outer punch (or his upper part) upwards. Then a further rise of the outer punch preferably is only caused by a lifting of the inner punch above the limit stop with respect to the outer punch or by a rise of the lower part of the outer punch exceeding the maximum spring travel of the upper part of the outer punch.

The limit stop constructions described in the prementioned embodiments can be realized in various ways. As to that, manifold possibilities are known to the expert. The limit stops can be realized not only within the lateral dimensions of the outer punch (as shown in drawing 19), but can be accommodated, for example, also outside of (for example, as shown in drawing 20) or inside the thickened guiding shaft of the punch.

A further possibility to realize the relocatability of the lower outer punch by pressure from above is the spring-loaded mounting of the outer punch with respect to the inner punch (see drawing 25, elements 12).

In a further embodiment with such a punch with integrated spring suspension its guide is carried out so that the outer punch is guided by guides arranged exteriorly of the lower punch only when it is not completely raised with respect to the inner punch.

This is achieved, for example, by the fact that the guide is designed so, that it has an effect on the guide bolt (or the guide element) of the outer punch only from above, for example, by use of a guide rail which is only arranged above the guide bolt.

A limitation of the spring travel with respect to the inner punch or the die can be realized as with the above described embodiments.

In another embodiment, with such a punch with integrated suspension this is carried out so that the outer punch is displaceable downwards even if it is guided unsprung via its guides arranged outside of the lower punch (or acting on the lower part of the outer punch), This guide then limited its displaceability only upwards. Downwards, it is limited by a limit stop with respect to the inner punch. For this purpose, the outer punch is preferably carried out at least two-part (see drawing 26 elements 1B and 1B2).

This embodiment permits, for example, the use of rotary presses, which are designed for two-part lower punches without the punch guides would have to be modified. Also in this embodiment, a limitation of the spring travel with respect to the inner punch or the die can be realized as in the embodiments described above.

In a further embodiment with a punch with integrated spring suspension the punch is provided with a lock-in mechanism (drawing 23, element 13). By this lock-in mechanism the relocatability of the outer punch can be limited with respect to the inner punch. Alternatively the relocatability of the outer punch can be limited with respect to the die in similar manner.

In a further embodiment the relocatability of the outer punch with respect to the inner punch or the die is limited only upwards by the lock-in mechanism. Still the outer punch is slidable downwards due to pressure from above, at least up to a possibly present limit stop with respect to the inner punch, the die or a possibly present lower part of the outer punch.

The engaging and/or disengaging of the lock-in mechanism can be controlled via corresponding limit stops (plugs/operation elements), e.g., at the guide tracks of the lower punch. Thus the lock-in mechanism can be activated (armed) before the second pressing step, so that the outer punch engages in the not raised position with the second pressing step. Preferably the lock-in mechanism is disengaged after the last pressing step or after the ejection step, so that the outer punch can be raised again by the spring-loaded bearing with the next first filling step.

In a further embodiment with a punch with integrated spring suspension and lock-in mechanism the lock-in mechanism is carried out so, that it is engaged and/or disengaged by the movements of the outer punch with respect to the inner punch. This can be realized, for example, by a push-push mechanism like it is also used with ballpoint pens to alternately bring the refill into an extended or retracted position by repeated pressure of the operation button (see, e.g., http://www.lehrerfreund.de/technik/1s/kugelschreiber/3078, archived on 30 May 2013 at http://www.webcitation.org/6H0dgMhHv). The lock-in mechanism is, for instance, so constructed, that the outer punch (e.g., with a cog ring 16 integrated into it) corresponds to the handle pipe of the ballpoint pen and the parts of the inner punch correspond to the operation button (lower part 1A3) and mine (middle part 1A2 and upper part 1A1) with the pressure sleeve (17) lying in between (see drawings 27-36). By corresponding implementation of the interlocking it is possible to carry out the lock-in mechanism in such a way, that it only engages with every third or higher numbered operation (by the vertical movement of the lower outer punch caused by the upper punch) in order to be able to carry out two or more filling steps before, with the last filling step, the side walls are filled at the same time. With a preferred embodiment the lock-in mechanism is carried out in a way that it can engage with several operations in two or more individual positions, depending on how many filling- and pressing steps are necessary for the production of the molding. Thereby, for instance, it is possible, to adjust individual filling amounts for every filling step by an individually adjusted height of the inner punch for every filling step, while the upper edge of the outer punch is level with the upper edge of the die. The realization of individual lock-in positions can be achieved by different heights or positions of the cogs in the sprocket of the lock-in mechanism which is for instance arranged in the shaft of the outer punch (analogously of the handle pipe of the ballpoint pen). The number of the positions can be determined by the number of the cogs and notches of the push-push mechanism and the number of the repetitions. For instance, the lock-in mechanism is carried out with twelve cogs/notches and three consecutive individual positions are repeated four times. Push-push mechanisms with ballpoint pens are usually carried out with eight cogs/notches and two consecutive individual positions (mine retracted and extended) are repeated four times.

In a further embodiment with a punch with integrated spring suspension and lock-in mechanism the lock-in mechanism is carried out in a way that it is engaged and/or disengaged by the movements of the outer punch with respect to the die. Again, individual positions are possible, for instance as they are described with the embodiment with activation by movements of the outer punch with respect to the inner punch.

In a further embodiment two or more lock-in mechanisms are used which are engaged and/or disengaged either by movements of the outer punch with respect to the inner punch or by the movements of the outer punch with respect to the die where not all lock-in mechanisms need to be triggered by the same movement.

In such an embodiment, for instance, two lock-in mechanisms are used, one of which is engaged and/or disengaged by movements of the outer punch with respect to the inner punch and the other by the movements of the outer punch with respect to the die.

If the lock-in mechanism is carried out in a way that the outer punch engages with respect to the inner punch, after it was moved downwards by the pressure carried out by the upper punch relatively to the inner punch, it possibly cannot engage so far downwards as it would be necessary to bring its upper edge level with the upper edge of the inner punch. For the first filling- and pressing step and the filling- and pressing steps with which core material is filled this is usually not critical. However, with the last filling- and pressing step, with which usually also the side walls are filled and compressed, this can be problematic as because of this, with the filling step the raw material cannot get towards the height of the lower punch beside the core. However, with cover layers with great layer thickness a part of the filled raw material is pressed downwards by the upper punch, also along the sides of the core, because the outer punch is pressed further downwards by the pressing pressure. But then, depending on the geometry of the upper punch, the raw material at the side of the core is, perhaps, compressed less strongly than below and above the core. Nevertheless, with many applications this is uncritical and can be compensated, if applicable, by a ratio of the side wall thickness to base plate thickness of more than 1:1.

In order that that the filling space can also be filled at the side of the previously compressed partial molding, it is advantageous to lower the outer punch with respect to the inner punch further than only up to the upper edge of the previously compressed partial molding, which is why a further embodiment of the invention proposes that.

An embodiment achieves this further lowering by the fact that the upper punch is also carried out as a multi-part punch, and the upper outer punch is shifted downwards with respect to the upper inner punch, but can be moved upwards again by pressure from below, until a predefined shift with respect to the upper inner punch is achieved, which can be zero, but also slightly negative, for example, in order to realize the previously described better sealing the filling space with the pressing step (see drawing 37). The spring force with which the upper outer punch is pressed downwards is preferably higher than the spring force which presses the lower outer punch upwards, so that the lower outer punch can be pressed downwards by the upper outer punch so far that, for example with the second pressing step a lock-in can be achieved approximately on height of the lower inner punch or also below it. However, preferably it is lower than the pressing pressure with the last pressing step, so that the mentioned predefined shift, with respect to the inner punch, is achieved before the molding is pressed into its final shape.

An embodiment achieves this further lowering by the fact that the upper punch is also carried out as a multi-part punch, and the upper inner punch is shiftable upwards by a certain measure with respect to the upper outer punch by pressure from below (see drawing 38). Through this, with the pressing step the lower edge of the upper outer punch can get further downwards than the lower edge of the upper inner punch by this measure than and at this press the lower outer punch further downwards.

According to a further embodiment the upwards directed slidability of the upper inner punch can be blocked by a lock-in mechanism or the like, so that the last pressing step can be pressed with unshifted upper punch. A corresponding lock-in mechanism can be implemented similarly to the lock-in mechanisms in the lower punches.

A further embodiment achieves the further lowering of the lower outer punch by the fact that the upper part of an at least two-part lower inner punch is shiftable downwards with respect to its lower part upon pressure from above by a certain amount (see drawings 28-36). This can be realized, for example, by the use of a spring (element 14) and two limit stops (element 15 and the parts of the upper part of the lower punch which are hitting it from below and above). Due to this slidability upon pressure from above the outer punch can be shifted further downwards by a level upper punch, because due to the slidability also the upper part of the inner punch and therefore the upper edge of the partial molding can be shifted further downwards. After the lock-in mechanism is engaged and has fixed the outer punch relative to the lower part of the inner punch (or with alternative embodiments with respect to the die or the die plate), the upper part of the inner punch is moved back upwards by the spring during the following raising of the upper punch. If the amount of this shift is adjusted according to the height of the partial molding (and the mechanical hysteresis of the lock-in mechanism), the upper edges of the outer punch and the inner punch afterwards are on the required relative height to each other, so that with the next filling step the raw material for the side walls can be filled also beside the core. The spring force, with which the upper part of the lower inner punch is pushed upwards, is preferably similar to the spring force, with which the outer punch (or its upper part) is pushed upwards when its surface is level with that of the inner punch. Because of this, with the last pressing step an uniformly as possible lowering of both lower partial punches and a flattest possible underside of the molding result. With embodiments with which the outer punch before the last filling step engages somewhat lower than the inner punch, for example, in order to be able to fill in more raw material for the side walls, both spring forces and spring characteristics (e.g., progressivity) preferably are selected so that both of the lower part punches have taken their final position relative to each other, before the side walls are compressed by more than the square root of their final compression factor. If the material of the side walls is compressed, for example, by a factor of 1.44:1, both lower part punches should have taken their final position relative to each other, before the side walls are compressed by more than factor 1.2:1.

A further embodiment achieves the further lowering by the fact that the lock-in mechanism fixes the outer punch relative to the die. If, before or during the second pressing step, the inner punch is lowered further than it is required for the next filling step, by about the height of the molding thereby produced (if applicable even slightly further in order to compensate for the mechanical hysteresis of the lock-in mechanism), the outer punch can be fixed by the lock-in mechanism in the required position. By the subsequent raising of the inner punch by the corresponding amount, the upper edges of the outer punch and the inner punch are at the desired relative height to each other, so that with the next filling step the raw material for the side walls can be filled also beside the core.

A further embodiment achieves the further lowering by the fact that the lock-in mechanism fixes the outer punch with respect to the die only temporarily. With this embodiment, before or during the second pressing step the inner punch is lowered further than it is necessary for the next filling step by somewhat more than the height of the at the same time produced partial molding, and the outer punch is fixed then with respect to the die. With the next raising of the inner punch the outer punch engages in the desired position with respect to the inner punch and preferably at the same time the lock-in with respect to the die is disengaged.

This embodiment has the advantage that the position of the lower punch at the second filling step is not limited by the fixation of the outer punch to the die.

With the embodiments with lock-in mechanism, the engaged lock-in mechanism preferably is loosened (disengaged) after the last pressing step or with or after the ejection step. This can happen, for example, by actuation elements which are mounted at or near the punch guides, and which loosen the lock-in mechanism while passing the punch.

With a further embodiment the lock-in mechanism is disengaged when the lower (outer) punch has penetrated further into the die than it penetrates with the third filling- and pressing step. Preferably then, when it penetrates so far into the die that its upper edge reaches at least the height of the upper edge of the die (as it is the case with the ejection step).

A variation of this embodiment disengages the lock-in mechanism only when the punch is lowered again after the ejection step, so that the molding is not ejected too high by the spring forces suddenly again having an effect on the outer punch.

With a further embodiment the lock-in mechanism is disengaged when the lower punch, after previous engaging of the lock-in mechanism, is once again loaded with a pressure from above which exceeds a certain measure. For instance, with the embodiment with the at least two-part lower inner punch whose upper part is mounted spring-loaded, the lock-in mechanism is disengaged if the outer punch is once again lowered with respect to the lower inner punch by a certain measure (e.g., by a push-push lock-in mechanism as described above).

With a further embodiment the lock-in mechanism is disengaged if the lower punch is lowered downwards by a certain amount. This can be advantageously combined with the fact that after the ejection step the lower punch is lowered so far downwards that its upper edge is lowered below the lower edge of the die, so that the punch surface can be cleaned from remaining raw material by brushing, blow off or other cleansing steps. For example, the lock-in mechanism can be disengaged by the fact that a lever is triggered once it is moved while lowering the punch against the mounting of the punches.

With a further embodiment, with the last filling step the outer punch is shifted with respect to the inner punch so far that its upper edge lies under the upper edge of the latter. Through this more raw material for the side walls can be filled in. This is advantageous if the lower compressibility of the precompressed core is to be accounted for and/or a stronger compression of the side walls is to be achieved. With the subsequent pressing step the outer punch is raised back relative to the inner punch so far that the upper edge of the inner punch and the one of the outer punch are level, so that the molding gets an even underside. The relative raising of the outer punch can be also achieved by a relative lowering of the inner punch. Hereto, preferential measures, as for example the selection of the spring forces, are described in the previously described embodiments.

With a further embodiment the outer punch is also lowerable with respect to the inner punch further than it is required for the last pressing and filling step, however, only with a pressure which is higher than the pressing pressure with the last pressing step. This can be realized in that the limit stop, which limits the slidability of the outer punch with respect to the inner punch downwards, is also mounted spring-loaded, however, with an accordingly high spring force. By such an embodiment, for example, an ejection step can be realized, with which the molding is expelled out of the die by raising of the upper edge of the lower inner punch above the upper edge of the die, although the maximum height of the upper edge of the outer punch, is limited, for example, for the first filling steps, to the height of the upper edge of the die.

With the embodiments with which the outer punch engages slightly deeper than the inner punch (measured at their upper edges) before the last filling step, for example, to be able to fill in more raw material for the side walls, this measure by which the outer punch engages deeper, preferably amounts to maximum 40% of the total height of the finished molding, more preferred maximum 20% of the total height of the finished molding, even more preferred maximum 10% of the total height of the finished molding.

Depending on elasticity and plasticity of the used powder mixtures or granulate materials a more or less strong adhesion of the molding or the partial molding on the die wall or the inner wall of the lower outer punch can happen. This can be disadvantageous in particular when it occurs with the first pressing step, or with pressing steps, with which the lower outer punch is moved downwards and after which it is moved back upwards, because then perhaps the partial molding is also moved upwards with the lower outer punch and the filling space cannot be filled correctly with the next filling step.

In order to avoid this, in a further embodiment with such pressing steps an as low as possible pressing pressure is used, so that a leveling of the already filled material takes place in order to avoid a mixing with the material to be filled in afterwards, but the already filled material is not pressed on to the inner wall of the lower outer punch so strongly that the partial form part moves upwards together with the lower outer punch with the subsequent upward movement of the latter.

In a further embodiment it is dispensed with one or several pressing steps, namely with the pressing steps with which the lower outer punch would be moved downwards after which he would be moved back upwards. For example, it is dispensed with the compression of the first layer of the shell material.

A further embodiment of the invention intends that one or several intermediate punches (20) are used. An intermediate punch is a punch which is inserted between the upper and the lower punch, preferably above the die or die disk.

In an embodiment at least an intermediate punch in its bottom has a shape which in its lateral dimensions substantially corresponds to the upper end of the lower inner punch, so that with a downward movement it can compress a material filled within the lower outer punch against the lower inner punch, without the lower outer punch having to be moved downwards at the same time.

At its upper end the intermediate punch has a structure which preferably is suitable for that with a downward movement the upper punch touches down onto it and with a further downward movement presses the intermediate punch downwards. The structure can be also decorated in such a way that the upper punch penetrates at least in some cases into them, for example, to enable a better guide of the intermediate punch.

This structure can consist of a level surface. Preferably it is adapted to the geometry of the upper punch. For example, the upper structure of the intermediate punch, in the area in which the upper punch touches down on it, can be carried out convex if the upper punch has a concave pressing surface.

This structure can consist from a material which is softer, than the upper punch, or be coated with such a material, so that the pressing surface of the upper punch possibly does not become damaged on impact on the structure.

The vertical power transmission of the upper punch to the intermediate punch can also take place through other structures than the pressing surface of the upper punch; it can take place, for example, by keyways, springs, bars and other kinds of the mechanical coupling. Through this, for example, the punch surface of the upper punch can be spared, because it does not have to come into contact with the intermediate punch.

With a further embodiment the ring-shaped horizontal surface (drawings 39 and 40, 30, viewed from below) is used for this purpose (for the vertical power transmission) which arises at the position at which the upper punch has a staged reduction of its diameter (drawings 39 and 40, 31). Above this reduction of the diameter the punch has a greater diameter which corresponds approximately to the diameter of the guide sleeves of the punch mounting. This part corresponds to the guiding shaft (drawings 39 and 40, 29, cutaway view of the upper punch viewed from the side)

Below this reduction of the diameter the punch has a smaller diameter which corresponds approximately to the diameter of the molding to be produced.

The intermediate punch (drawing 40, 32) has, at the upper end, a pipe-shaped structure into whose hollow cavity the upper punch dives with its pressing surface (drawings 39 and 40, 28) and its accordingly dimensioned lower part, and on whose upper ring-shaped surface (drawing 40, 33, view from above) puts on the ring-shaped surface of the upper punch (drawing 40, 26, cutaway view from the side, upper punch touched down on intermediate punch).

With a further embodiment the tubular structure has a lateral orifice (drawing 41, 34, views from below, from the side and from above). Preferably this lateral orifice consists of a vertical slot which extends up to the ring-shaped upper surface and has a width which is at least so great, as the diameter of the lower, tapered part of the upper punch.

Through this it is possible to position the intermediate punch under the ring-shaped surface of the upper punch from the side without having to raise the upper punch so far that its pressing surface has to be completely above the intermediate punch.

With embodiments with or without lateral orifice the pipe-shaped structure preferably can be carried out tapered at its bottom, in particular conically tapered downwards (drawing 42, 35). Particularly preferred no further tapering takes place at the same time once the outside diameter of the lower end of the upper punch is reached.

Preferably, with the positioning of the intermediate punch below the upper punch from the side, the pressing surface of the upper punch preferably is positioned above the point with the greatest tapering but below the place with the biggest tapering after the downward movement of the upper punch up to the contact of both ring-shaped surfaces.

Particularly preferred a present lateral orifice does not extend below the point with the greatest tapering.

With such embodiments an especially good centering of upper punch and intermediate punch can be achieved.

If an intermediate punch is inserted below the upper punch, with a downward movement of the upper punch it is pressed and also moved downwards by the latter. Then it dives into the die orifice and can compress the material located there below its pressing surface (e.g., shown in drawing 40, 27, view as seen from below).

With or after an upward movement of the upper punch the intermediate punch is also moved again upwards.

This can take place through a mounting/holder (21 and 22) of the intermediate punch spring-loaded in the vertical direction or through other suitable means as, for example, by a pneumatic cylinder or hydraulic cylinder, a control cam like the cam for the upper and lower punches.

An intermediate punch preferably is inserted below the upper punch only for certain sub steps.

Drawings 30 and 31 show the arrangement of the intermediate punch (20) below the upper punch (2) in its mounting/holder (21) in which a spring suspension (22) keeps the intermediate punch up if it is not pressed downwards by the upper punch, or raises the intermediate punch again, after it had been pressed downwards by the upper punch and the upper punch exerts no more pressure on the intermediate punch. Here the pressing step of the first layer of the shell material is shown.

The mechanics for the positioning of the mounting/holder of the intermediate punch is not shown in these drawings. It can be carried out, for example, as above described by means of rotor, chain or in other ways.

Preferably an intermediate punch is inserted below the upper punch if the first layer of the shell material is to be compressed.

With a further embodiment an intermediate punch is inserted below the upper punch if the first layer of the shell material is to be compressed and if one or several layers of core material are to be compressed and if further layers are to be compressed between these layers.

With a further embodiment an intermediate punch is inserted below the upper punch if only material within the lower outer punch is to be compressed.

With a further embodiment an intermediate punch is inserted below the upper punch always then when only material within the lower outer punch is to be compressed, except with the last one of these pressing steps. Thereby with this step it can be achieved that also the lower outer punch is moved downwards during the pressing step. Because of this it can be dispensed with separate guide tracks for the lower outer punch.

With further embodiments an intermediate punch is so carried out that its pressing surface (the lateral dimensions) corresponds to the combined pressing surfaces of lower inner punch and outer punch, and the upper punch is so carried out that his pressing surface corresponds to the pressing surface of the lower inner punch. With these embodiments this intermediate punch is inserted only with the steps with which no intermediate punch is inserted with the above described embodiments. On this occasion, in principle, the pressing surface dimensions and pressing steps of upper punch and intermediate punch are exchanged. This can be advantageous particularly if a greater number of pressing steps are to be carried out with raised lower outer punch.

With further embodiments several different intermediate punches are used for different pressing steps.

For example, for the compression of the first layer of the shell material an intermediate punch is used that has a convex pressing surface which has a similar or a somewhat smaller bulge radius as the concave pressing surface of the lower inner punch. For the compression of the core material an intermediate punch is used which has a concave pressing surface which has a similar or a somewhat smaller bulge radius as the concave pressing surface of the upper punch. Preferably the concave bulge of the lower inner punch continues in the pressing surface of the lower outer punch.

By use of such an embodiment with which the pressing surface of the lower outer punch is not level but rises towards the outside, it can be achieved that during the compression the shell material, which is filled around the core, is pressed against the prepressed shell material of the first layer by the outwardly rising pressing surface of the lower outer punch and thus a better containment of the core material is achieved.

The insertion or positioning of the intermediate punch below the upper punch preferably is carried out by a lateral movement of the intermediate punch.

For example, with a compression molding apparatus with which upper and lower punch are not moved laterally, e.g. an eccentric press (Korsch XPI) vis-à-vis the filling shoe, which is moved laterally across the die orifice for filling of the material to be compressed and is retracted afterwards, a device is arranged, which, similar to the movement of the filling shoe, positions the intermediate punch above the die orifice where it then can be moved downwards by the upper punch. Preferably the intermediate punch is mounted spring-loaded upwards (meaning that the bearing applies a spring force on the intermediate punch which presses it upwards) in a holder which is moved across the die orifice with the intermediate punch. The drawings 30 and 31 show a corresponding mounting (21) with intermediate punch (20). After the upper punch and the intermediate punch are raised again, the intermediate punch is moved away from the die orifice, preferably together with its mounting.

Instead of a linear movement of the intermediate punch and its mounting, a movement can also take place on a partial circle trajectory, e.g. if intermediate punches and holder are mounted on a cantilever which is fixed to an axis which runs in parallel with the die orifice. Intermediate punches and bearing are moved laterally to below the upper punch or removed from below it by rotation of the axis or rotation of the cantilever around the axis.

With compression molding apparatuses with which upper and lower punch are also moved lateral, as for example with a rotary press, with which the lateral movement preferably corresponds to a circular path, the intermediate punch or the intermediate punches preferably are positioned below the corresponding upper punch along a partial circle of this circular path with the upper and lower punches and are carried along there synchronically.

Then during the movement along this section of the circular path preferably the downward movement of the upper punch and with it also a downward movement of the corresponding intermediate punch and a compression of material located within the die orifice or within the lower outer punch take place.

Also with this positioning below the upper punch the intermediate punch preferably is mounted upwards spring-loaded in a holder which also is carried along synchronically.

The synchronous entrainment of the intermediate punch and/or its mounting along a certain section (partial circle) of the circular path of upper and lower punch (circular punch path) can be achieved via different embodiments.

In some embodiments the synchronous entrainment takes place via a sort of chain, like it is used also in EP2165826A2 in order to synchronically carry along the holders used there for the tablet cores (there referred to as "core retention elements" 52). Though in EP2165826A2 no intermediate punches, as they are used in the present invention, are carried along synchronically with the upper and lower punches, but "core retention elements" which for the implementation of the present invention, however, can be replaced with core punches with mountings, so that after a corresponding exchange, in principle, the construction of the entrainment described in EP2165826A2 can be also used for the present invention.

Herewith reference is made expressly to EP2165826A2 and the corresponding implementations in it. In particular reference is made to the paragraphs [0035] to [0037] and [0041] to [0043] as well as the drawings named therein.

The "core push pin" (58) described therein preferably is replaced by an intermediate punch. The "core holder" (57) described therein preferably is replaced by an upwardly spring-loaded mounting for the intermediate punch. This can for example consist of a stack of disc springs. The outer shape of the "core retention elements" can largely be maintained, including the "transfer cog" (56), which is suitable for the synchronous entrainment of the intermediate punch with the upper punch.

Preferably, however, the "transfer cog" is not completely open at the bottom, but has only an orifice there, which is slightly larger than the lower part (the shaft at the lower end) of the intermediate punch, so that it is guided laterally therein. The annular surface of the underside of the "transfer cog", which has the orifice in which the lower part of the intermediate punch is guided, preferably also serves as an abutment of the upwardly spring-loaded mounting of the intermediate punch. A corresponding drawing of such an embodiment looks like drawing 9 of EP2165826A2, except that:

1. The cylindrical "core holder" (57) is replaced by a cylindrical disk spring stack and
2. the "transfer cog" on its underside has a surface on which the disk spring stack rests, the surface on the underside of the "transfer cog" having an orifice which is slightly larger than the lower part of the intermediate punch so that it can protrude and
3. the "core push pin" is replaced by the intermediate punch, which has approximately the shape of the "core push pin", but has a pressing surface on its underside with which shell and/or core material can be compressed.

In further embodiments, the synchronous entrainment takes place via a rotor as it is used EP0349777A1 (marked there with number 10) in order to synchronically carry along the core punches used there together with the tablet cores hold by them. In EP0349777A1 indeed no intermediate punches, as used in the present invention, are synchronously entrained with the upper and lower punches, but transfer heads (8) with core punches, which, however, can be replaced by core punches with mountings so that after an appropriate exchange the construction of the entrainment described in EP0349777A1 in principle can be used for the present invention.

Herewith, reference is made expressly to EP0349777A1 and the corresponding explanations therein. In particular, reference is made to the description from page 3, column 3, line 25 to page 4, column 5, line 24, page 4, column 6, lines 1 to 37, page 5, column 7, line 42 to page 5, column 8, line 20.

Similar to the second embodiment, which is described in EP0349777A1 (page 5, column 8, line 21 to page 7, column 11, line 44), the intermediate dies can be moved downwards also via the lowering their holders as it is realized in EP0349777A1 with the cylinder piston units (111). In particular, if no high pressing forces are required, as it may be the case, for example, during the compression of the first layer of shell material, this is a practical embodiment.

Preferably, the synchronous entrainment is also carried out across more than two adjacent dies.

In principle, both embodiments of EP0349777A1 can be modified, so that embodiments of the present invention may be carried out with them.

The core punches are replaced by intermediate punches, which have pressing surfaces at their underside, with which shell and/or core material can be compressed.

The vacuum technique of EP0349777A1 can be dispensed with, since no cores have to be supplied. Also, the guiding device can be omitted.

Instead of filling tablet cores in the die orifices, material, filled into the die orifice or within the lower outer punch beforehand, is compressed by the downward movement of the synchronically carried along intermediate punches.

A further possibility to synchronically carry along one or several intermediate punches with one or several upper punches consists in fixing the holder or the holders for the intermediate punch(es) at the mounting or the mountings for the upper punches or the lower punches or the die or its mounting. Through this the intermediate punch or the intermediate punches basically move synchronically to the upper punches.

Via a possibility to move an intermediate punch sideways, it can be positioned below the upper punch or besides it if required (with a rotary press, for example, outside or within the orbiting circle described by the upper punch or in the space between two neighboring upper punches).

A preferred embodiment implements this by vertically oriented profiles attached to the periphery of the disk-shaped upper punch guide, which extend downward to the height of the interspace between the die and the pressing surface of the raised upper punch.

Preferably, one such profile is applied per punch.

From below a swiveling mounted, preferably horizontally arranged profile is attached to each of these profiles, and preferably the vertical profile or the attachment to the vertical profile constitutes the axis of rotation for the horizontal profile. To this profile, preferably at its end, the holder for the intermediate punch is attached or worked in into it. The intermediate punch can be swung in or out under the upper punch by rotation of the horizontal profile. Preferably the rotation is limited by limit stops, for example, to an angle area which encloses 60 degrees. Preferably the horizontally arranged profile is fixed to one of both positions (swung in or swung out) by a spring, so that for a change of the positions a force effect is necessary only in one direction (or just the absence of this force effect).

The positioning (swung in or out) can be carried out in various ways. For example, the profile can be implemented as L-shaped angle, whose one arm carries the holder of the intermediate punch and whose other arm (guide leg) is at an angle of about 120 degrees with respect to the first arm. If the profile is fixed by the spring in the swung out position, the arm with the holder for the intermediate punch is aligned tangentially to the die plate and the other arm radially outward. By a largely circular guide track, which is arranged at the height of the horizontal profile, and has a nominal diameter which is greater than the diameter of the orbiting circle of the vertical profiles by the length of the guide arm, and whose diameter is reduced at certain locations, the horizontal profile can rotate in the swung-in position for a partial circle of the orbiting circle (FIG. 46).

Instead of a fixing to the perimeter of the disk-shaped upper punch guide a fixing is also possible at the underside of the upper punch guide, for example, also further inside than the upper punches are guided.

Then, if applicable, the guide way can be attached also further inside and then interferes less with the operation of the press.

The above-described horizontal profile can also be fixed to a rotatable shaft.

This shaft can, for example, be guided upwards by the vertical profiles described above. Preferably the position (swung in or out) is determined by rotation of this shaft. The rotation can be determined, for example, by a guiding track which preferably is located above the upper punch guide.

A guiding of the shaft is as possible downwards of course. It can be also guided through the die disk. Then preferably it is turned according to a guiding track which is located below the die disk.

Alternatively a radially shiftable mounted profile, which then, for example, has a straight shape, can be also used instead of a rotatable mounted profile.

In another embodiment, horizontal profiles are mounted radially below the upper punch guide or above of the die table or the die disc, preferably one profile per upper punch. These profiles rotate around the vertical axis of the rotary press together with the punch guide, the die table or the die disc, but are mounted radially shiftable with respect to them.

The radial position of the profile is determined by a cam track. The cam track may also be attached outside the circular path described by the punches. Preferably, the cam is mounted within this circle. The cam is preferably stationary, i.e. preferably does not rotate around the vertical axis of the rotary press together with the punch guide, die table or the die disc. Preferably, the cam is mounted rotatable with respect to the vertical axis of the rotary press, so that the lateral position is fixed with respect to this axis. A co-rotation with the axis is prevented by a fixing to a stationary member of the press. In a preferred embodiment, this fixing is made at one or more filling shoes, or on its mounting or their mountings.

The horizontal profiles preferably are attached elevated with respect to the die table/the die disc, so that they do not collide with the filling shoe, the filling shoes or their mounting during the rotation around the axis. Therefore, with a preferred embodiment the attachment or mounting of the profiles takes place at mounting of the upper punches.

By corresponding pick-ups, which pick up the contour of the cam track, the radial position of the cam is transmitted to the profiles.

For example, the cam track consists of a disk having on its upper side a circumferential groove, into which engage pins which are mounted at the end of the profiles which is facing the axis. Because the distance of the groove to the axis differs depending on the angular position, the profiles are radially positioned corresponding to this distance. Due to this an intermediate punch arranged at the abaxial end of the profile can be arranged between the upper punch and the die and also be removed again accordingly from that position. With a further embodiment several intermediate punch holders with intermediate punches are attached to the profile.

Thus, by the distance of the groove to the axis and consequently the radial position of the respective profile one of several preferably different intermediate punches can be positioned between upper punch and die.

In a further embodiment, just before approaching the filling shoes until after passage of the same the profiles are shifted paraxial by a correspondingly designed curved track so far that a collision with the filling shoe or the filling shoes is precluded. Thus, the horizontal profiles can also be mounted on the die table/the die disc.

In some embodiments, the horizontal profiles are guided in a disc having radial grooves or slots in which the horizontal profiles are guided.

The radius of the disk preferably is not greater than the radius of the space between the axis and any parts which protrude into the space within the orbiting circle of the upper punch.

The radius also can be greater, but preferably not greater than the radius of the space between the axis and any stationary components which protrude into the space within the orbiting circle of the upper punch, for example, the filling shoes or the scraper. At the points at which co-orbiting components protrude further into this space, disc preferably is recessed.

Since the disc also rotates around the axis, it may also be connected to other peripheral components in some embodiments.

In preferred embodiments, a rotor comprises an upper punch holder, a middle section with integrated or thereto attached die plate and a lower punch holder.

Above the die disc the middle section has two radial bores per punch pair which are arranged above each other. In the bores two radial part arms are guided, which are mounted radially shiftable in the bores. The abaxial ends of these part arms are connected to one or several intermediate punch holders and preferably are so fixed thereon that they cannot turn around their longitudinal axis. Thereby the one or several intermediate punch holders are so fixed that they cannot be tilted around one of their axes and that the intermediate punches hold therein are always oriented vertically. They merely, together with the rotor, rotate around its axis and are shiftable radially via the also radial shiftably mounted radial part arms.

Via guide elements, preferably via pins which are fixed to a part of the radial part arms, the intermediate punch holders are positioned at a specified radial position depending on the position of their orbit around the axis (angular position). For example, they are positioned directly below the respective upper punch if an intermediate punch is to be used for compression at this angular position. Accordingly, they are positioned more towards the axis when no intermediate punch is to be used for compression at this angular position. If more than one intermediate punch holders are attached to a radial arm, it is determined by the radial positioning, whether a, and if so, which intermediate punch is used at this angular position.

Preferably there is a certain distance between the die plate and the vertical position of the lower hole in the middle section so that between the die plate and the lower part arm there is room for components not rotating with the rotor.

Preferably, in this space a cam disc is arranged. This is, for example, a disc, which rests on the die disc sliding, with rollers, balls, or mounted in any other way, and is so fixed that it does not rotate with the rotor. For example, the cam disc is attached to the filling shoes. It may, instead of resting on the die plate, be held in a circumferential groove of the middle section at a defined height. Also it can be held below the upper punch holder by an appropriate mechanical construction.

In certain preferential embodiments, this cam disc has on its upper side a groove which has a defined distance to the axis depending on the angular position. In this groove the guide elements of the radial adjustable arms engage. Preferably these guide elements consist of pins which either are mounted rotatable within the radial arms or have a rotatable wheel at the end diving in the groove of the cam disc (if applicable in the form of a simple ball bearing), so that the friction between the guide elements and the side walls of the groove is minimized.

In other embodiments the cam disc has a not circular perimeter instead of a groove. The radius of the cam disc is at the same time depending on the angular position. With such embodiments the guide elements do not reach into a groove, but are in contact with the perimeter of the cam disc. In addition they are, similar to the above described embodiments, either mounted rotatable in the radial arms or have a rotatably mounted wheel at that end, which is guided along the perimeter of the cam disc.

Preferably the guide elements protrude only to a part of the thickness of the cam disc into it, or are guided only on a part of the vertical perimeter surface, so that the groove does not have to be as deep as the thickness of the cam disc, or the vertical perimeter surface does not have to be available over its whole height.

For example, the deepness of the groove in the cam disc corresponds to two thirds of its thickness and the guide elements dive into the groove to half of the cam disc thickness.

Preferably, the cam disc is mounted glidably or otherwise rotatable with respect to the middle section, so that it is not laterally shiftable relative to it.

Preferably it is carried out two-part or multi-part. For example, it consists of two semi-circular disks with semi-circular cut-outs for the middle section, which are brought towards the middle section from two opposite sides and are then fixed to each other.

In further embodiments the cam disc can be arranged also in a hollow cavity within the rotor. For example, it is arranged between the axis around which the rotor turns and the middle section of the rotor. The radial arms at whiches abaxial side the intermediate punch holder is arranged are guided in radial bores through the wall of the rotor into this hollow cavity and shifted there radially, depending on the perimeter of the cam disc which preferably is fixed to the axis. For this purpose, with the help of springs the radial arms are pressed in the direction of the axis so far, until they bottom out there. Preferably a friction of the arms on the cam disc is avoided by supporting rolls.

In further embodiments the radial arms have a noncircular cross section. Thereby they are not twistable in the guiding bores even if they consist of single profiles. Therefore no two or more part arms are necessary with such embodiments.

To the expert other methods are also known how he can carry out and guide the arms torsion-proof.

Such an embodiment of the invention is explained in more detail in the following with the help of an execution example pictured in the drawings. It show:

FIG. 61 a vertical section through the compression molding apparatus for producing core moldings when the intermediate punch is retracted, FIG. 62 a vertical section through the compression molding apparatus for producing core moldings with an intermediate punch arranged below the upper punch and pressed downwards by it, FIG. 63 a principal horizontal cross section through the press with an embodiment with two intermediate punches and their holders, each.

The press for producing core moldings comprises a rotor 1 being fixed to a rotating drive shaft 51, and an upper punch section 52, a lower punch section 53 with a die table 54 fixed therebetween, and a stationary curved bell 55 with a cam disk 56 and an upper punch guide cam 57. The curved bell 55 is fixed in the structure, and the drive shaft 51 is supported within the curved bell 55 by means of bearings not shown in detail.

The rotor 50 comprises a circular support plate 58 mounted onto the drive shaft 51, the annular lower section 53 being rigidly attached to said support plate. The heads 60 of the lower punches 59 are guided in a manner not shown in more detail, in order to affect a vertical up and down movement of the punches 59. Onto the lower section 53 is mounted the circular disk-shaped die table 54. The latter comprises a partial circle 61 for the dies 62 and a free space 63 having a smaller diameter than the partial circle 61 for the dies 62.

Above the lower section 53 and the die table 54, there is provided an upper section 52 attached at the rotor 50. The upper section serves for guiding the upper punches 64 being supported in guide bushings 65 within the upper section 52. The heads 66 of the upper punches 64 are guided in the upper punch guide cam 57, which is fastened to the fixed curved bell 55. The support plate 58 welded to the drive shaft 51 is rigidly connected with a welded-on support cylinder 67 arranged concentrically with the axis of the drive shaft 51. The support cylinder 67 forming an internal support for the upper section 52 and the lower section 53 of the rotor 50.

On the curved bell 55, the cam disk 56 is fixed by means of threaded bolts. The base body, forming the cam disk 56 at its lower section, is disposed concentrically to the drive shaft 51. The shape of the cam disk 56 results from the cross section according to FIG. 63. Radial arms 70 are operated by the cam disk 56. The radial arms being adapted as piston having a polygonal profile 71, and being supported, radially with respect to the axis of the drive shaft 51, in bushings 72 radially mounted in the upper section 52 and having a polygonal profile. For passing the pistons through, the support cylinder 67 of the rotor 50 has radial through-orifices. At the radially inwardly disposed end of the piston, support rolls 73 are supported over antifriction bearings, in particular needle bearings, in receiving slots. The rolls 73 being rotatable on a bearing pin 74 disposed transversely to the longitudinal axis of the piston. On the side disposed radially outwardly of each bearing pin 74, there is supported a limiting disk 75 for a compression spring 76. The spring 76 rests against the front radially inwardly directed of the polygonal bushings 72, and affects a permanent press-on force for the support roll 73 on the outer curve of the cam disk 56.

The press shown in the figures carries, on the table 54, twenty four (24) dies 62 with respective lower and upper punches 59, 64, and with respective radial arms 70 in the form of pistons. Each piston carries at its radially outward, free end an intermediate punch holder 77 (FIG. 63 depicts an embodiment with two intermediate punch holders each). Each intermediate punch holder 77 comprises a head section provided with a bore for receiving the piston. The head section is non-rotatably and non-displaceably fixed at the piston. Transversely to the longitudinal direction of the piston, and parallel to the axis 51' of the drive shaft 51 extends an intermediate punch 78 serving for compressing first shell material and core material. The intermediate punch 78 penetrates a lower bore of the head section provided with a slide guiding, and is further guided by a collar sliding, in the upper section of the head section, in an internal bore. In the internal bore of the head section, at the upper end thereof, an annular disk is fixed by means of a circlip. Between the collar of the intermediate punch 78 and the bottom of the internal bore of the head section extends a compression spring affecting a permanent pressure of the collar of the intermediate punch 78 against the annular disk.

The mode of operation of the press described above for producing core moldings is described hereinafter.

After filling the die with a first shell material, a radially outward movement of the intermediate punch holder 77 into the partial circle 61 of the dies 62 is performed by the cam disk 56 and the compression spring 76 associated thereto. The intermediate punch is now below an upper punch and above a die 62 for compressing. The first shell material present within the die 62 on the lower punch 59 is now compressed in by means of the intermediate punch. For this purpose, the intermediate punch 78 is pressed in, under the action of the upper punch 64 against the action of the compression spring. Subsequently, the upper punch 64 is lifted under the action of the upper punch cam 57, and simultaneously, the intermediate punch 78 is guided out of the die 62 under the action of the compression spring. Then, under the action of the cam disk 56 and of the inwardly pushing compression spring 76 the piston is moved radially inwardly, and another radial introduction of the intermediate punch holder 77 into the free space 63 takes place. The free space 63 being located radially inwardly outside the area of the dies 62 being in the partial circle 61. In this position of the intermediate punch holder 77, now the filling of the die with the core material can be performed. Subsequently, under the action of the cam disk 56 and of the inwardly pushing compression spring 76 the intermediate punch holder 77 is moved radially outwardly into the area of the dies 62 being located on the partial circle 61. The core material being present within the die on the already compressed first shell material is now compressed with the help of the intermediate punch upon action of the upper punch. With embodiments with several intermediate punch holders 77 per radial arm each, with this press step a different intermediate punch is used than with the previous compression of the first shell material. For this purpose, for instance, the radial arm is extended more or less in order to position the required intermediate punch below the upper punch. Subsequently, under the action of the cam disk 56 and of the inwardly pushing compression spring 76 the intermediate punch holder 77 is once again moved radially inwardly into the free space 63. In this position of the intermediate punch holder 77 the filling of the die with the second shell material and, afterwards, upon action of lower and upper punches 59, 64, the last pressing step of the compression molding apparatus can be performed.

The radial arms described can also be arranged in such a way that they do not run exactly radially, but at a slight angle, so to speak tangentially of a circle concentric to the axis of the rotor, which is smaller than the orbiting circle of the upper punches. This allows a longer guiding of the arms being made possible, for example if the diameter of the central part is relatively small or the diameter of the axis is relatively large.

Preferably the horizontal profiles or the radial arms comprise several holders for intermediate punches and can be positioned on more than two positions. Thus several different intermediate punches can be used.

The previously described I-shaped profile can be Y-shaped, for example, and have two holders with intermediate punches. Then depending on the guiding track (or on its diameter at certain partial circles) the first, the second or none of the intermediate punches is positioned below the upper punch.

A positioning of the intermediate punch (no matter whether by rotation or other movement) can also take place through magnets, hydraulics, pneumatics or other mechanics.

With embodiments with intermediate punch, preferentially it can be dispensed with the spring-loaded mounting of the lower outer punch, in particular if, for filling and compression of the second layer of the shell material, the lower outer punch can be moved downwards by other measures, for example, by separate guiding tracks.

It can be advantageous to move the intermediate punch back upwards after the pressing step not only via the spring-loaded mounting. In addition to or instead of the spring-loaded mounting the raising of the intermediate punch can also take place by other measures.

In the further embodiments, preferably those which otherwise correspond to the previously described embodiment with the synchronous entrainment of the intermediate punches by a chain (based on the co-guiding of the "core retention elements" used in EP2165826A2), the mounting of the intermediate punch comprises two rings which lie level on top of each other. Both rings have, on their axial sides facing each other, saw teeth like with a hirth coupling which are complementary to each other and therefore can interlock. One of the rings, preferably the lower ring, is mounted rotatable at its vertical axis. Preferably this ring lies on the bottom of the "transfer cog" with its level axial side. The second ring lies upon the first ring with its cogged axial side and is not rotatable with respect to the transfer cog. For example, it has radial guide pins at its perimeter which bite in vertical notches on the inside of the transfer cog. Thus, it can be moved upwards.

If the lower, rotatably mounted ring is turned, the cogs of both rings are no longer complementary to each other, so that the upper ring is moved upward. This movement is based on the same mechanism as with stroke element (4) of EP1158207B1 which is herewith taken reference to regarding the stroke mechanics.

This upwards movement of the upper ring, forcibly raises the intermediate punch, or supports the lifting effect of the spring-loaded mounting.

Preferably spring-loaded mounting and rota-lift-mechanics are combined. For example, the rings have a substantially larger internal diameter than the intermediate punch diameter at the lower end. This results in, a cylindrical cavity between the inner punch and the rings, in which the spring can be arranged.

Preferably the lower ring also has cogs at its perimeter, which can be used through holes in the transfer cog by means of a pin, penetrating from the outside in order to move the ring into rotation. Corresponding pins are, for example, located in the recesses of the back cog wheel (the last one passed by the chain), which presses the chain against the partial circle of the die table and serves for the redirection of the chain.

If a transfer cog reaches the redirecting cogwheel, its pin stings through the holes, turns the lower ring and thereby raises the intermediate punch.

In a further embodiment, another cogwheel is arranged before the last redirecting cogwheel which has corresponding pins and so raises the intermediate punch already before the redirecting cogwheel.

A further possibility to raise the intermediate punch consists in it being raised via a guide track which does not turn with the rotor.

On that account, preferably corresponding diagonal ramps are arranged at the places of the orbiting circle at which a rise is necessary. The intermediate punch then has a guiding stub which, once the intermediate punch is guided past the ramp rests on it and is moved upwards by it.

A further possibility to raise the intermediate punch is, to couple it mechanically with the corresponding upper punch while it synchronously passes along the partial circle so that it is also raised with the upward movement of the latter.

In a further embodiment a circumferential notch (drawing 43, 36) is worked into the upper punch, for the possibility of the lifting of the intermediate punch by the upper punch. A tongue in the intermediate punch (drawing 43, 37) bites in this notch and allows the upper punch to take along the intermediate punch with it downwards movements, as well as upward movements.

Preferably the downwards entrainment of the intermediate punch happens not via notch and tongue, but via the ring-shaped area described to begin with, at the point where the upper punch is tapered. This allows a larger contact area so a better power transmission can be achieved during the pressing.

Alternatively a tongue which fits in a notch at the intermediate punch can also be circumferential around the upper punch.

Alternative fits are possible and can be carried out by the skilled person without having to be inventively active.

An execution example is shown in drawing 43.

Above the lower end of its guide shaft, the upper punch has a circumferential notch (36).

At its upper end the intermediate punch (38) has a pipe-shaped structure whose inner diameter is slightly larger than the diameter of the guide shaft of the upper punch.

A ring-shaped, or on account of the lateral orifice a rather half-ring-shaped tongue (37) allows the vertical raising of the intermediate punch by the upper punch in whose notch (36) the tongue bites. Drawing 43 shows the central section, seen from the side with the lateral orifice. The upper punch is lowered, centered, and can now move the intermediate punch downwards.

Drawing 44 shows the intermediate Punch seen from the side with the lateral orifice.

Drawing 45 shows the upper punch and the intermediate punch seen from the side with the lateral orifice, with the upper punch in the not yet lowered position in which the intermediate punch can be positioned below the upper punch from the side (in this view from the back) and also be removed.

In other embodiments, particularly those embodiments in which the pressing surface of the intermediate punch is greater than the pressing surface of the upper punch, the pressing surface of the intermediate punch may have a recess, into which the lower part of the upper punch protrudes from above. Thus, then pressing surface of the upper punch and the pressing surface of the intermediate punch form a joint press surface. In such embodiments, the lower portion of the upper punch preferably does not protrude so far into the recess of the intermediate punch that its pressing surface is at its outer periphery lower than the inner edge of the pressing surface of the intermediate punch.

Preferably, however, the press surface of the upper punch does not come into contact with the material to be pressed, if an intermediate punch is positioned below the upper punch. Particularly preferably this is ensured by the fact that the upper punch cannot protrude through a recess in an intermediate punch.

Embodiments with one or more intermediate punches can be carried out both together with spring-loaded mounted lower punches, with or without their own punch guiding tracks, as well as with unsprung lower punches, which are then preferably guided by their own punch guiding tracks.

In further embodiments, the filling and pressing of a first layer of shell material is dispensed with. Thus, at first core material is filled and compressed with raised outer lower punch and lowered inner lower punch (FIGS. 47 and 48).

Then, during, before or after filling the shell material, the lower outer punch is lowered so far that its upper edge is lowered below the upper edge of the lower inner punch, and/or the inner punch is raised accordingly far before, during or after this filling step. Preferably, the lower inner punch is raised (FIG. 50) after the filling step (FIG. 49). Preferably the raising takes place while the filling device still is located above the die orifice, so that material emerging out of the die is pushed back into the filling device and does not get lost. Shell material is thereby at the side of the lower inner punch located also below the compressed core material by which a kind of skirt 47 made of shell material is created. If thereafter the inner lower punch is lowered, a cavity 48 (FIG. 51) is created below the already compressed core material, because the compressed core material is hindered from following the punch downwards by the shell material filled around it. In order that the already compressed core material does not sink downwards together with the lower inner punch, it can be necessary that the shell material being sideways thereof is being slightly compressed beforehand and thereby being pressed towards the core material. For this in a preferred embodiment the lower outer punch is raised before lowering the lower inner punch, preferably by one third, more preferred by half of the height of the skirt. Meanwhile, in order to prevent an upward evasion of the shell material in a further preferred embodiment the upper punch is landed on the shell material. Preferably the inner lower punch is lowered so far that its pressing surface is flush with that of the outer lower punch.

Then the lower punch is raised (FIG. 52). In the course of this the skirt consisting of uncompressed shell material breaks apart during this upward movement of the lower punch and the broken apart shell material 49 spreads on the pressing surface of the lower punch by which a layer of compressible shell material is located also below the compressed core material and a core molding is created with the further raising of the lower punch (FIG. 53). Alternatively to or together with the raising of the lower punch the upper punch can be also lowered in order to let the material of the skirt become broken and to push into the cavity. Afterwards the entire tablet is compressed and ejected.

In further embodiments, an at least three-part coaxial lower punch is used which has, in addition to the two-part lower punch an outermost lower punch. With such embodiments, core moldings can be prepared, with which the core is double coated.

The outermost punch remains raised and its pressing surface level with the upper edge of the die, until a core molding is produced using one of the methods described above, which is referred to as an inner core molding.

The inner lower punch and the outer lower punch then act like the inner lower punch in the immediately preceding embodiment in which the filling and compressing of a first layer of shell material is dispensed with. The outermost lower punch acts accordingly like the outer lower punch in the immediately preceding embodiment. The already produced inner core molding acts according to the already compressed core material.

After the compression of the inner core molding, during, before or after filling in the shell material, the lower outermost punch is lowered so far that its upper edge is lowered below the upper edge of the inner and outer lower punch, and/or the inner and the outer lower punch are raised accordingly far before, during or after this filling step. Shell material is thereby at the side of the outer lower punch located also below the inner core molding by which a kind of skirt made of shell material is created. If thereafter the inner and outer lower punch are lowered, a cavity originates below the inner core molding, because the inner core molding is hindered from following the punch downwards by the shell material filled around it. Preferably, inner and outer lower punch are lowered so far that their pressing surfaces are flush with that of the outermost lower punch.

Then, the entire lower punch is raised. In the course of this the skirt, consisting of the uncompressed shell material, falls or breaks apart during this upward movement of the lower punch, and the shell material is spread on the pressing surface of the lower punch, by which a layer of compressible shell material is located below the inner core molding. Alternatively to or together with the raising of the lower punch, the upper punch can be also lowered, in order to let the material of the skirt become broken and to push it into the cavity. In a preferred embodiment, the pressing surface of the lower punch is designed concavely, or at least the pressing surface of the outermost lower punch is beveled inwardly (towards the inner punch). This allows for the spreading below the inner core molding of a part of the shell material, which had formed the skirt, to be supported.

Afterwards the entire tablet is compressed and ejected.

In this way, even moldings with double-coated cores can be produced.

For example, drug granules or drug-containing micro pellets are used as core material, granules of polyvinyl diethylaminoacetate (AEA Sankyo), if applicable with additives, as the first shell material, granules of shellac, if applicable with additives, as a second shell material, and granules of Eudragit L, if applicable with additives, as a last shell material. The tablets produced in this way release the active ingredient or ingredients in the colon of a human.

If the granules of active ingredient or the active ingredient-containing micropellets are coated beforehand with a polymer that is insoluble above pH 7 but soluble below pH 6.5, such as, for example, chitosan, a release prior to reaching the large intestine can be prevented even more securely, which is why this represents a preferred embodiment.

With embodiments with a three-part coaxial lower punch the vertical positioning of the three partial punches is realized, for example, by means of three separate guiding tracks (guide curves).

With preferred embodiments with a three-part coaxial lower punch, the vertical positioning of at least one of the three partial punches is carried out using a spring-loaded mounting with lock-in mechanism so that preferably no more than two guiding tracks are required for the lower punches.

With an embodiment, the upper punch, or the corresponding intermediate punch, which is used with the last pressing step for the inner core molding, has a pressing surface, the lateral dimensions of which correspond to the lateral dimensions of the outermost lower punch. In addition to compressing the inner core molding it thus also moves downwards the outermost lower punch, which is spring-loaded mounted. In this downwards moved position the outermost lower punch locks, for example, relative to the die.

After the filling of the material for the outermost shell, the inner and outer lower punch are lifted in order to position the inner core molding upwards into the filled material. The outermost lower punch remains lowered, so that the material filled above it is not moved upwards together with the inner core molding, but remains sideways of the latter one and sideways of the lower outer punch. A part of the filled material located above the inner core molding flows to the side and ensures that also sideways of the raised inner core filled in molding material is present. Thereafter, the inner and outer lower punch are lowered again in order to create a cavity under the inner core molding. With this downward movement the locking of the outermost lower punch moves from a lock-in relative to the die to a lock-in relative to the inner and outer lower punch. Preferably, in this lock-in position the pressing surfaces of the three partial punches form a common pressure surface corresponding to the desired geometry of the lower side of the core molding.

If this has not already happened during the lowering of the inner and outer lower punch, with the subsequent raising of the lower punch the material sideways of the cavity falls inwardly onto the pressing surface of the lower punch and is compressed into the bottom part of the outermost shell during the further raising. The material located sideways from the inner core molding is pressed into the side part of the outermost shell, the material located above the inner core molding is pressed into the upper part of the outermost shell.

Example description of an embodiment of the lock-in mechanisms:

The outermost punch (St) locks with respect to a tube (Ro 2) which is pressed in the direction of the die (Ma) via a spring (Fe1). A stronger, pretense spring (Fe2) keeps a certain distance between the tube Ro2 and the die, as long as the force pressing the pipe Ro2 upward, does not exceed the pretense force of the spring Fe2. Between the pretense spring Fe2 and the die is a further disc Sc1 arranged, which is attached to a further tube Ro3, which extends over the punch shaft (Sh1), where it is hooked so that the path of the tube Ro2, the pretense spring Fe2 and the outermost punch St1 is limited upwards when the lower punch is moved down.

By pressure from above the outermost punch is pressed down and engages there, so it stays down when the pressure from above is removed. On renewed pressure from above the outermost punch disengages, or the rotor engages in a further upwards adjustable position, and can be moved further upwards again. This is achieved, for example, by a lock-in mechanism, as it is used in ballpoint pens, for example, by a lock-in mechanism with a rotor. The rotor is pushed upwards by a spring, and thus also presses upwards the outermost punch, the height being precisely determined by the engagement of the rotor into the guide grooves on the inside of the tube Ro2, and this height being alternating between two predetermined heights.

The way upwards of the outermost punch is limited by a limit stop by the die or the disc Sc1, so that the top edge of the outermost punch cannot extend above the top edge of the die.

If the tube Ro2 is pressed upwards with a greater force than the pretense force of the pretense spring Fe2, the pretense spring Fe2 is compressed and the outermost punch St1 now moves downwards relative to tube Ro2 because due to disk S1 it cannot move further upwards together with Ro2. Thereby, the lock-in mechanism between the outermost punch and tube Ro2 is released again. Tube Ro2 is spring-mounted with respect to the outer punch (with spring pressure upwards upon Ro2). Ro2 can be moved upwards by the outer punch. This is done via a second lock-in mechanism. In the basic state, this second lock-in mechanism is locked in in a way that the pressing surface of the outer punch can be raised above the pressing surface of the outermost punch. This enables for the inner core molding, after the filling of the filling material for the outermost shell layer, to be raised into this shell material and to create a kind of skirt around the outer punch made of coating material, since a part of the coating material slips laterally past the inner core molding and just a part of it remains above the inner core molding With this raising the second lock-in mechanism is pre-activated. Once the outer punch is lowered in order to create a cavity below the inner core molding, the second lock-in mechanism is engaged in a way, that with the raising of the outer punch the tube Ro2 follows it to an extent that the pressing surface of the outermost punch in its lower locked-in position of the first lock-in mechanism is flush with the pressing surfaces of the outer and inner punch and with these forms a common pressing surface.

On the subsequent raising of the outer punch the outermost punch follows the same. The skirt of shell material collapses, as it is mechanically loaded from below by the upwardly moving lower punch and is not supported from the side due to the cavity below the inner core molding, and can serve as a lower layer of the outer shell. Once the core molding is finally compressed, it is ejected by the outer punch being raised so that its pressing surface is raised above the upper edge of the die. Since the outermost punch cannot be moved upwards so far that its pressing surface would extend over the die, it is moved downwards relatively to the tube R2, moving upwards together with the outer punch which disengages its locking mechanism and ensures that it remains flush with the upper edge of the die flush even after lowering the outer punch, since then again it can be pressed upwards by the spring Fe3. Upon further lifting the outer punch the second latching mechanism is pre-activated for the disengagement, so that it disengages with the lowering of the outer punch below the outermost punch.

In further embodiments, an undivided lower punch is used. Similar as described in "A Novel Compression-Coated Tablet Dosage Form", Madhusudan Hariharan and Vishal K. Gupta, Pharmaceutical Technology YEARBOOK 2001, a cup-shaped molding of shell material is first created. For this purpose, however, no two-part coaxial upper punch is used, the inner punch of which is moved downwards relative to the outer punch, but an intermediate punch that has a corresponding shape (outer diameter of the entire pressing surface corresponding to the outer diameter of the lower punch having a partial pressing surface tapered by the wall thickness of the cup-shaped molding to be molded and projecting downwards by about the depth of the trough of the cup-shaped molding to be molded). The lower partial pressing surface of the intermediate punch can be conically shaped (slightly tapered) in order to press a part of the filled shell material outwards so that the side walls of the cup-shaped part to be formed can be built. Similarly, the upper annular partial pressing surface may be shaped slightly tapered in order to let the upper edge of said side walls taper inwardly downwards at a slight angle, so that subsequently filled in core material is to slip off them below is and to fall into the trough of the cup-shaped part.

Then, the core material is filled in and preferably pressed into the trough with an additional intermediate punch. Thereafter, shell material is filled in for the upper shell layer. This is compressed with an additional intermediate punch or the upper punch.

Since during the compression of the core material, filled in after the generation of the cup-shaped molding, another intermediate punch can be used, the pressing surface of the latter can be shaped differently. Likewise, the pressing surface of the upper punch may be shaped differently than that of the intermediate punch or punches. This makes it possible to form these pressing surfaces flat or slightly concave or hollow-cone-like. This is the subject of a further embodiment of the invention. In contrast to the method as described in "A Novel Compression Coated Tablet Dosage Form", Madhusudan Hariharan and Vishal K. Gupta, Pharmaceutical Technology YEAR BOOK 2001, with which tablets are produced, which are convex or conical at one side, but concave or concave-conically at the other side, herewith tablets can be produced which are plane, biconvex or plano-convex, or conical on both sides.

In addition to a freer shaping, in doing so the lower and upper layers of shell material (base and lid of the core molding) can be also produced with a particularly uniform thickness. Among other things, for example, the abrasion at sharp tablets edges is reduced, which may, for example, occur at the top edge of tablets, which, like in "A Novel Compression Coated Tablet Dosage Form" are compressed by means of a cone-shaped punch with the last pressing step.

In further embodiments a special die is used, making it possible to dispense with the use of a coaxial lower punch, or with an otherwise necessary three-part coaxial lower punch a two-part coaxial lower punch is sufficient. This die has in its orifice a tubular insert, which is vertically displaceable. Preferably, the displaceability of the tubular insert is limited at least in one direction.

Particularly preferably, the displaceability of the tubular insert is limited in both directions. The limitation of displaceability preferably is realized by one or more limit stops. Preferably, the special die is carried out as a die insert which can be inserted into a corresponding bore in the die plate. Similar die inserts are known in the art. Usually, they consist of a cylindrical disk, which has a vertical bore in its center, which serves as a die for the molding to be pressed.

Around the disk there is a circumferential groove, which corresponds to a mounting hole in the die plate, through which a retaining pin is screwed, which engages with its tip in the groove of the die insert, presses the die insert against the opposite wall of the bore in the die plate, and thus fixes the die insert within the die plate.

The special die insert (FIG. 46), with respect to the outer shape, corresponds to the conventional die inserts, and thus consists of a disc-shaped body 40. The diameter of the bore (die hole) and its shape correspond to the outer diameter and the shape of the molding to be pressed. However, it has a tubular insert 43, whose outer diameter is slightly smaller than the diameter of the bore in the die insert, so that it can be moved vertically therein. The inner diameter corresponds to the core diameter of the molding to be pressed. In principle, the tubular insert corresponds to the tip of the outer lower punch, as used with the use of coaxial lower punches. The lower punch, which is used in such embodiments, corresponds to the inner lower punch, as used with the use of coaxial lower punches. In FIG. 46 the gap between the inner wall of the die bore and the tubular insert is shown wider than it is usually carried out in order to be visible on the drawing.

The die insert preferably is designed so that the tubular insert can be displaced vertically only when a vertical force is applied on it, which exceeds a certain level. This can be achieved by various measures. For example, when using a circular hole in the die insert the tubular insert is not completely circular at its outer periphery, but slightly oval, having two external diameters, one of which is slightly smaller than the hole in the die insert and the other a little more slightly larger. Also, the inside circumference is then preferably slightly oval, with the axes of the ovals being corresponding to each other, but the difference between the maximum and minimum inner diameter being less great than the one between the maximum and minimum outer diameters. For the insertion of the tubular insert into the bore of the die insert it is compressed at the opposite cylindrical side surfaces with the maximum diameter, so that under tension it takes on a substantially circular form and can be inserted into the bore. There it retrogrades back into its oval shape as far as possible and then with the opposite cylindrical lateral surfaces with the maximum diameter it abuts to the inner wall of the bore and is fixed in its vertical position by the resulting friction, so that it can only be moved vertically with respect to the die insert if the force acting on it exceeds the static friction.

The static friction force can be adjusted by the shaping and the material properties. In the FIGS. 54 to 60 some steps of the method with such a tubular insert are shown. There also is shown how the tubular insert is moved downwards by the upper punch and upwards by the lower punch once they abut at the tubular insert with their region increased in diameter and overcome the static friction with their onward movement.

In a further embodiment the die insert has a further bore from its underside which is coaxial with the die hole but has a larger diameter or larger dimensions. This hole is only so deep that the die bore is maintained in its original diameter at least up to the maximum filling depth of material to be compressed. Preferably at the lower end of this bore a means for the insertion or fixation of a closing disc 44 is provided, for example, an internal thread. There a closing disk can be inserted, which also has a bore which preferably corresponds to the die bore. The tubular insert comprises a region in which the outer diameter is increased, but no greater than the diameter of the above described hole in the bottom of the die insert. Said region is preferably as far away from the upper end of the tubular insert so that the top of the tubular insert is flush with the top edge of the die insert when the tubular insert abuts with the upper end of the region at the end of the enlarged bore, whereby the displacement path of the tubular insert is limited upwardly. The region is preferably as far away from the lower end of the tubular insert, so that the upper edge of the tubular insert is still above the end of the enlarged bore when the tubular insert with the lower end of the region abuts against the closing disc, by which the displacement of the tubular insert is limited downwards.

The die insert is preferably designed so that the tubular insert can be displaced vertically only when a vertical force is applied on it which exceeds a certain level. This can be achieved by various measures. For example, the tubular insert can be so deformed as in the previously described embodiment that it rubs against the wall of the die.

In a preferred embodiment, a kind of friction brake is arranged in the gap between the wall of the enlarged bore in the die insert and the region of the tubular insert which has an enlarged outer diameter, respectively. This preferably consists of a strip of spring-loaded material, for example a strip of spring steel sheet which is wave-shaped and is pressed into the gap while being shaped into an open ring.

In another embodiment, one or more bores are formed in the die insert that lead from the perimeter surface forth radially to the enlarged bore. In these holes brake elements 41 are inserted, for example, cylindrical rods made of a material with a defined static friction against the material of the tubular insert. Arranged radially farther outwards are spring elements 39, for example, coil springs and one or more closing pieces 45, for example, grub screws. The spring elements fixed outwards by the closing pieces press the brake elements against the enlarged diameter region of the tubular insert and allow its vertical movement only when the axial force acting on it exceeds the static friction.

The static friction is preferably such that the tubular insert will only move when it is moved by contact with an upper punch, lower punch or intermediate punch and that one's further movement towards the tubular insert.

The tubular insert is thus moved downwards only by an upper or intermediate punch, the diameter of which is larger than the inner diameter of the tubular insert.

It is moved upwards only by a lower punch, the diameter of which is larger than the inner diameter of the tubular insert, or by an enlarged diameter region of the lower punch, if the diameter of the lower punch itself or its pressing surface is not greater Typically, the lower punch, which comes to use in such embodiments with a special die insert, has a region which is larger in diameter than its pressing surface. The vertical distance of this region to the outer edge of its pressing surface is preferably equal to the length of the tubular insert. Thus, the tubular insert is always moves upward by the lower punch when the pressing surface of the lower punch is level with the top of the tubular insert, and the lower punch further moves upwards.

In a preferred embodiment, a spring suspension 46, preferably in the form of a plate spring is inserted between the end of the enlarged bore and the top end of the region of the tubular insert having an enlarged diameter. Preferably, the bias of the spring suspension is so strong that it will not be exceeded under normal pressing steps, for example by interaction of an upward movement of the lower punch with the adhesion of the compression molding to the inner wall of the tubular insert. However, if the lower punch is raised so far that the region where its diameter is increased with respect to the pressing surface, has a smaller distance to the upper edge of the die insert, than the length of the tubular insert, the spring assembly is compressed, and the upper edge of the tubular insert elevates above the upper edge of the die insert, preferably with the pressing surface of the lower punch. This can be advantageous with the ejection step, since with this one the pressing surface of the lower punch should preferably at least be flush with the upper edge of the die insert. Due to unavoidable tolerances, it may happen that with the discharge step the upper punch is raised so far that its pressing surface extends a little bit over the upper edge of the die insert. If the stop of the tubular insert would not be spring loaded accordingly, it could lead to an excessive load upon the limit stop, the tubular insert, the lower punch or the die insert. Under certain circumstances, the lower punch would loosen the die insert from its fixation.

Due to the spring suspension of the limit stop the tubular insert can follow the movement of the lower punch and excessive stress on mechanical components can be avoided.

Preferably, one or more further bores 42 are formed in the die insert, which run from the space between the die hole or the enlarged bore and the tubular insert downwards to the bottom of the die insert. Through these bores filling material, which enters into the die insert through the gap between the die hole and the tubular insert, can escape downwards.

In further embodiments, no single die inserts are used, but the holes in the die plate are carried out corresponding to the above described holes in the die inserts and the tubular inserts or other types of structures are directly arranged in the die plate or incorporated into it.

In embodiments with which a special die insert is used according to the above-described embodiments, preferably no coaxial lower punch is used. With such embodiments, at the beginning of the method for the production of a molding with a core the tubular insert with its upper edge is flush with the upper edge of the die insert. According to the method with a coaxial lower punch the first shell layer and the core layer are filled and pressed. If applicable, further core layers and intermediate layers are filled and pressed. With the last of these pressing steps an upper punch or intermediate punch is used, which either has a pressing surface directly corresponding to the outer contour of the tubular insert, or which, slightly above the pressing surface corresponding to the inner contour of the tubular insert, has a region with an increase of the diameter which corresponds to the outer contour of the tubular insert. With this pressing step, the upper punch or intermediate punch is moved so far downwards that it moves the tubular insert downwards with its pressing surface or the underside of the enlarged diameter region. The lower punch recedes downwards so far that the compression preferably is complete only when the upper edge of the tubular insert is moved so far downwards that the above-fillable amount of second shell material is sufficient for the formation of the lateral and upper shell layer. After raising of the upper punch or intermediate punch the resulting cavity is filled with the second shell material, preferably by the die being carried along underneath a filling shoe. During the filling the lower punch is moved upwards, so that the two-layer or multilayer partial molding is also moved upwards. This makes it displace upwards some of the already filled in second shell material. The already filled second shell material located laterally thereof prevents decentering of the partial molding. The tubular insert does not move upwards or downwards at this, because it is hindered, for example, by the brake elements. As soon as the upper edge of the lower punch is flush with the upper edge of the tubular insert, the tubular insert is uniformly moved upward with it. For example, for this purpose, the lower punch has an increase of its diameter below its pressing surface. The increased diameter corresponds to the outer dimension of the tubular insert in the region not increased in diameter.

The distance between the pressing surface and the enlargement of the lower punch preferably corresponds to the length of the tubular insert. Overfilled second shell material is thereby pushed back into the feed shoe. By the amount of the raising, the amount of second shell material remaining in the die can be adjusted. Thereafter, the upper punch, the pressing surface of which corresponds to the outer contour of the tubular insert or a corresponding intermediate punch is lowered and the second shell material is compressed above and sideways around the partial molding. Because of the contact with the enlarged diameter region of the lower punch the tubular insert cannot escape downwards, thus its upper (e.g., annular) surface together with the pressing surface of the lower punch is forming a common lower pressing surface in size and shape of the molding to be produced. During the subsequent ejection step, the lower punch is raised so far that its pressing surface is raised at least up to the height of the upper edge of the die insert so that the core molding may preferably be extracted from the compression molding apparatus by means of a scraper. In doing so also the tubular insert is raised so far that a further pressing process can begin.

Embodiments in which the use of lock-in mechanisms is described may instead of being carried out with locking mechanisms also be carried out with specific utilization of friction forces, preferably with the usage of static friction forces. For example, instead of a described locking-in of the outer lower punch relative to the die also a friction of the shaft of the lower punch against the bottom punch guide can be used. Such uses of frictional forces are known in the art. For example, the vertical movement of the lower punch is braked with respect to its guiding in order to avoid a lifting off of the punch head off his guiding track after a fast raising action of the lower punch. In doing so, similar structures and methods are used, as described with the special die and the special die insert. The frictional forces can be adjusted, inter alia, by the materials used and their surface finish. Preferably, the adjusted static friction forces are greater than the frictional forces acting on the mechanical parts fixed by friction such as the outer lower punch or the tubular insert of the special die during the compression of shell or core material.

Particularly preferred embodiments are methods in which following compression molding apparatuses are used:

Compression molding apparatuses which can position an intermediate punch below the upper punch during a pressing step, with which the lower shell material and the (first) core material can be compressed at the same pressing step with the help of the intermediate punch, and with which the last pressing step is carried out without an intermediate punch being positioned below the upper punch.

Compression molding apparatuses which position an intermediate punch below the upper punch during a pressing step, with which the last pressing step is carried out with the help of the intermediate punch and with which the first layer of shell material and the core material are compressed in single pressing steps or in a common pressing step, without an intermediate punch being positioned below the upper punch.

Compression molding apparatuses which position intermediate punches below the upper punch with two or more pressing steps, with which the lower shell material and the core material and, if applicable, further layers of shell materials and core materials are compressed with the help of the intermediate punch or the intermediate punches and with which the last pressing step is carried out, without an intermediate punch being positioned below the upper punch.

Compression molding apparatuses which position intermediate punches below the upper punch with two or more pressing steps, with which the lower shell material and the core material and, if applicable, further layers of shell materials and core materials are compressed with the help of the intermediate punch or the intermediate punches and with which the last pressing step is also carried out with the help of an intermediate punch.

Prementioned compression molding apparatuses with which the lower punch or the lower punches are carried out at least two-part coaxially.

Prementioned compression molding apparatuses with which the lower punch or the lower punches are carried out not coaxially and with which the punch, being used with the pressing step used for the first filled shell material, is carried out so that while compressing it presses a trough into the filled shell material into which thereafter the core material can be filled.

Following Embodiments Also Are Particularly Preferred:

Methods for the production of a molding with a core under the use of a compression molding apparatus which comprises an upper punch and a lower punch which are arranged in vertical direction of a compression mold and at least one of the upper punch and the lower punch has a two-part structure which consists of an inner punch and an outer punch which surrounds the outer perimeter of the internal punch, with which the lower punch has an at least two-part structure which consists at least of an inner punch and an outer punch, which surrounds the outer perimeter of the inner punch and the outer punch is mounted spring-loaded with respect to the internal punch, with respect to the die or with respect to its guide.

Method as described above, with which the sequence of the method comprises the following steps:

A supply step 1 of the outer layer, with which molding material for a first part of an outer layer is supplied into a recess above the lower inner punch, which is enclosed by the lower outer punch;

a core supply step, in which the molding material for the core is supplied into a recess above the molding material for the first outer layer, which has been supplied in the preceding step, and enclosed by the lower outer punch;

a pressing step of the outer layer and the core, in which the molding material for the first outer layer and the molding material for the core supplied in the preceding steps, are compression-molded by the intermediate punch and the lower inner punch;

a supply step 2 of the outer layer, in which a molding material for a second part of the outer layer is supplied into a recess of a die above and around the first outer layer and the core, which have been formed in the preceding step, a complete pressing step, in which the first outer layer, the core and the molding material for the second outer layer, which has been supplied in the previous step are compression-molded by the lower and the upper punch; and a step of removing the compression-molded molding, which is carried out after the complete pressing step.

A method as described above, which between said supply step 1 and said core supply step comprises at least one pressing step of the outer layer, with which the molding material for the first outer layer is compression-molded.

Another preferred embodiment of the invention is a punch for the compression of a molding having an at least two-part structure consisting at least of an inner punch and an outer punch surrounding the outer periphery of the inner punch, said outer punch being mounted spring-loaded with respect to the inner punch, with respect to the die or with respect to its guide.

By using one or more, preferably different intermediate punches, it is possible to vary diameter, shape, contour, or other properties of the pressing surface acting from above on the inserted materials without having to change the actual upper punch or to use a multi-part coaxial upper punch.

An individual intermediate punch can be used with one, with several or with each of the different pressing steps in each case. With appropriate entrainment over a bigger section, intermediate punches can also be used for several pressing steps.

Preferably at least with one pressing step no intermediate punch is used (positioned below the upper punch). Thereby, the entrainment mechanics for the intermediate punch for at least one pressing step can be saved.

If the required properties of the pressing surface (diameter, shape, contour, etc.) are the same for several pressing steps, it is advantageous not to use intermediate punches for these pressing steps, but to compress directly with the upper punch, because then the number of required intermediate punches can be minimized.

It is advantageous not to use an intermediate punch for that pressing step, which requires the greatest pressing force. Thereby, the maximum mechanical load on the intermediate punches is reduced.

With the described embodiments of the invention it is possible, inter alia, to produce moldings with core, without being reliant on the upper punch having a two-part structure consisting of an inner punch and an outer punch and with which the outer punch surrounds the outer perimeter of the inner punch.

The embodiments with spring-loaded mounting are not limited to the use of springs, such as helical or plate springs, but can be carried out with any suitable kind of suspension. They can alternatively be carried out also by pneumatics or hydraulics. For example, plate spring stacks may be replaced by corresponding air pressure cylinder.

Word Definitions:

"Upper punch" essentially means the same as "upper punch".

"Lower punch" essentially means the same as "lower punch".

"Upper outer punch" and "upper outer punch" essentially mean the same as "outer upper punch".

"Upper inner punch" and "upper inner punch" essentially mean the same as "inner upper punch".

"Lower outer punch" and "lower outer punch" essentially mean the same as "outer lower punch".

"Lower inner punch" and "lower inner punch" essentially mean the same as "inner lower punch".

"Outer layer" means essentially the same as "shell layer", "shell" or "coating".

"Implementation" essentially means the same as "embodiment".

The drawings show various embodiments of the invention.

FIG. 1 shows the setting with the first filling step.
FIG. 3 shows, in addition, the filled shell material.
FIG. 5 shows the setting with the first pressing step.
FIG. 7 shows, in addition, the partial molding.
FIG. 2 shows the setting with the second filling step.
FIG. 4 shows, in addition, the filled core material.
FIG. 9 shows the setting with the second pressing step.
FIG. 11 shows, in addition, the partial molding.
FIG. 10 shows the setting with the third filling step.
FIG. 12 shows, in addition, the filled shell material.
FIG. 13 shows the setting with the third pressing step.
FIG. 14 shows, in addition, the molding.

The drawings show in each case cross sections of bodies of rotation (for the production of circularly cylindrical moldings). Except from this is the lock-in mechanism inserted into the punch from sideways (Element 13 in FIG. 23).

The springs illustrated can be implemented as plate springs, however, coil springs can be also used. The springs can be single springs running concentrically around the punch axis, as well as multiple spring elements distributed over the perimeter.

If not directly named differently, 1 denotes the lower punch (1A inner punch, 1B outer punch), 2 the upper punch, 3 the die, 4 the filling space, 5 the filled raw material or the molding or partial molding.

The remaining contents of the drawings are described in the text.

BRIEF DESCRIPTION OF THE DRAWINGS

FIG. 23 depicts the same as FIG. 21, but with a lock-in mechanism (13).

FIG. 24 depicts the same as FIG. 22, but with a spring-loaded limit-stop (7).

FIG. 27 depicts a lower punch (1A inner punch, 1B outer punch with an integrated cog ring (16, see corresponding reference in FIG. 32), a pressure sleeve (17, see corresponding reference in FIG. 33) and a lower part of the inner punch (1A3, see corresponding reference in FIG. 29)), a spring suspension (see FIG. 25, reference 12) of the outer punch being mounted with respect to the inner punch, a die (3), and a filling space (4).

FIG. 28 depicts a lower punch (upper part of the inner punch (1A1, see corresponding reference in FIG. 29), 1B outer punch with an integrated cog ring (16, see corresponding reference in FIG. 32), a pressure sleeve (17, see corresponding reference in FIG. 33) an middle part of the inner punch (1A2, see corresponding reference in FIG. 29) and a lower part of the inner punch (1A3, see corresponding reference in FIG. 29)), a spring suspension (see FIG. 25, reference 12) of the outer punch being mounted with respect to the inner punch, a spring-loaded limit-stop (see FIG. 24, reference 7), spring (see FIG. 29, reference 14) a die (3), two limit stops (see FIG. 29, reference 15 and FIG. 32, reference 15) and filled shell material (5).

FIG. 30 depicts the same parts as FIG. 28 but with addition of an intermediate punch (20), a holder (21) for the intermediate punch, and a spring suspension (22).

FIG. 31 depicts the same parts as FIG. 30 but in a different setting (with the first pressing step).

FIG. 32 depicts the same parts as FIG. 28 but in a different setting and with additional fill in material shown (5).

FIG. 33 depicts the same parts as FIG. 32 but in a different setting and with an upper punch (2) shown.

FIG. 34 depicts the same parts as FIG. 32 but in a different setting and with additional fill in material shown (5).

FIG. 35 depicts the same parts as FIG. 34 but in a different setting and with an upper punch (2) shown.

FIG. 37 depicts an upper part of FIG. 25 but with the upper punch carried out as a multi-part punch with the outer upper punch being spring-loaded.

FIG. 38 depicts an upper part of FIG. 26 but with the upper punch carried out as a multi-part punch with the inner upper punch being spring-loaded.

FIG. 39 depicts an intermediate punch viewed from below and the side.

Figure 1:
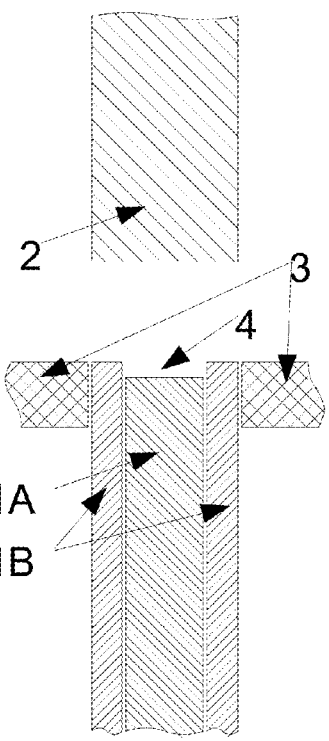
FIG. 1 depicts a lower punch (1A inner punch, 1B outer punch), an upper punch (2), a die (3), and a filling space (4) in a setting with the first filling step of an embodiment.
Figure 2:
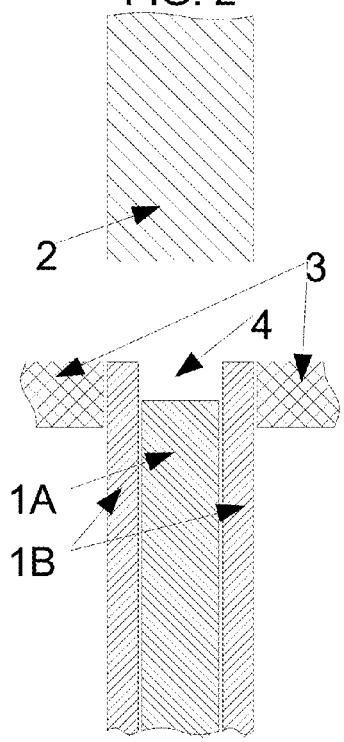
FIG. 2 depicts a lower punch (1A inner punch, 1B outer punch), an upper punch (2), a die (3), and a filling space (4) in a setting with the second filling step of an embodiment.
Figure 3:
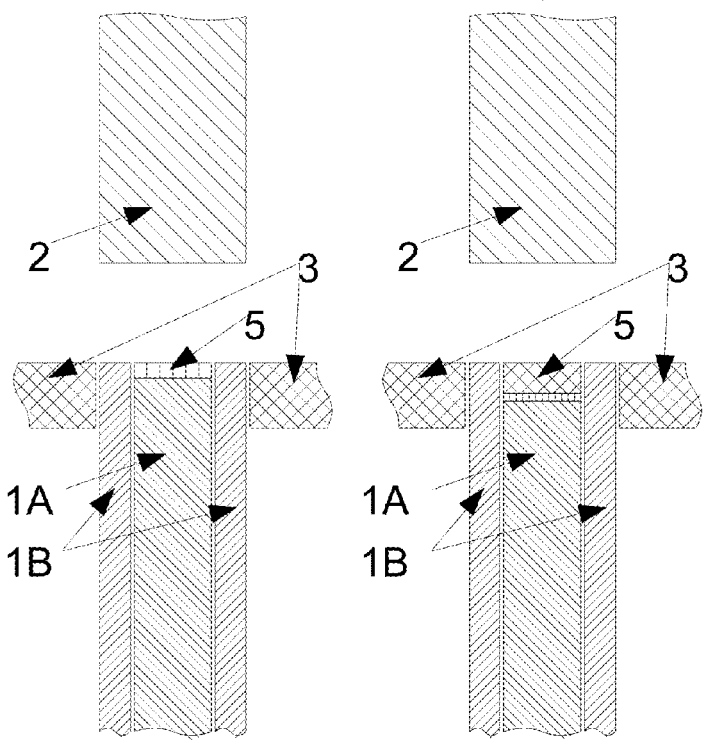
FIG. 3 depicts a lower punch (1A inner punch, 1B outer punch), an upper punch (2), a die (3), and filled shell material (5) in a setting with the first filling step of an embodiment.
Figure 4:
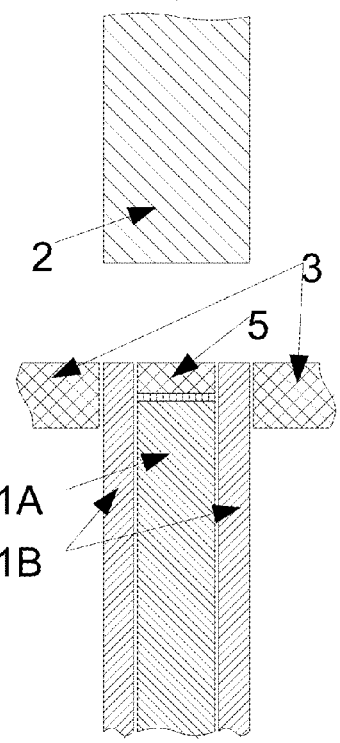
FIG. 4 depicts a lower punch (1A inner punch, 1B outer punch), an upper punch (2), a die (3), and shell and core material (5) in a setting with the second filling step of an embodiment.
Figure 5:
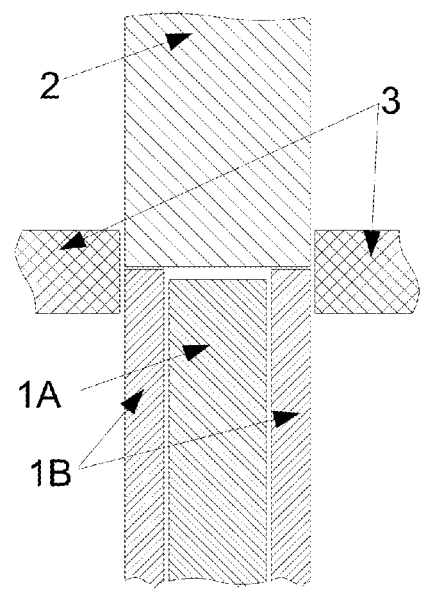
FIG. 5 depicts a lower punch (1A inner punch, 1B outer punch), an upper punch (2), and a die (3) in a setting with the first pressing step of an embodiment.
Figure 6:
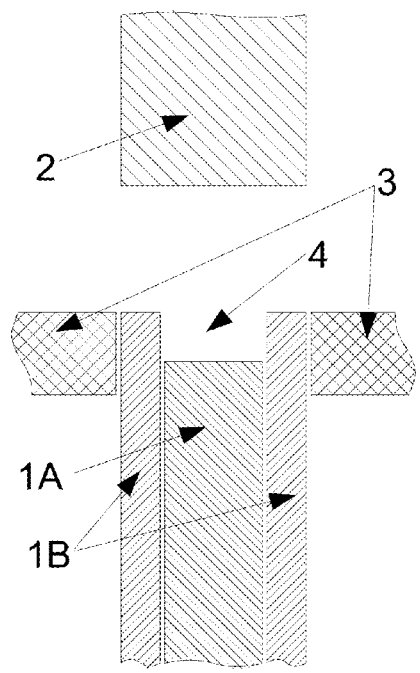
FIG. 6 depicts a lower punch (1A inner punch, 1B outer punch), an upper punch (2), a die (3) and a filling space (4) in a setting after the second pressing step of an embodiment.
Figure 7:
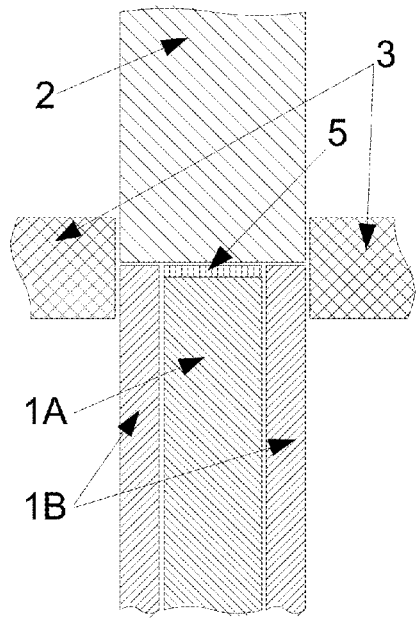
FIG. 7 depicts a lower punch (1A inner punch, 1B outer punch), an upper punch (2), a die (3), and filled shell material (5) in a setting with the first pressing step of an embodiment.
Figure 8:
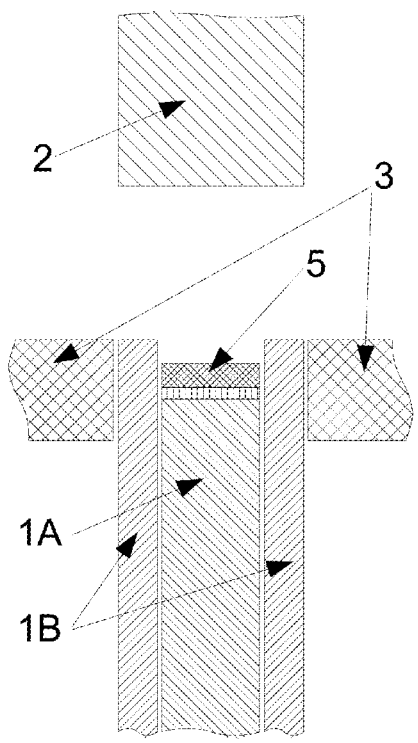
FIG. 8 depicts a lower punch (1A inner punch, 1B outer punch), an upper punch (2), a die (3) and shell and core material (5) in a setting after the second pressing step of an embodiment.
Figure 9:
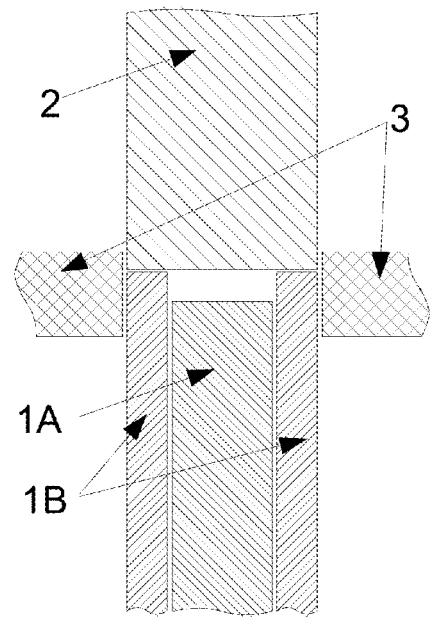
FIG. 9 depicts a lower punch (1A inner punch, 1B outer punch), an upper punch (2), and a die (3) in a setting with the second pressing step of an embodiment.
Figure 10:
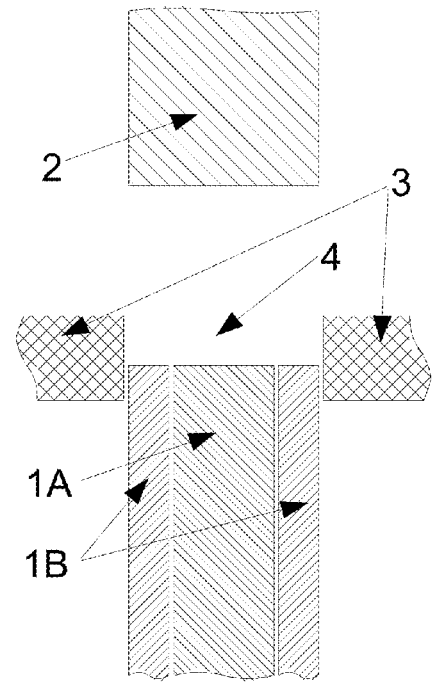
FIG. 10 depicts a lower punch (1A inner punch, 1B outer punch), an upper punch (2), a die (3), and a filling space (4) in a setting with the third filling step of an embodiment.
Figure 11:
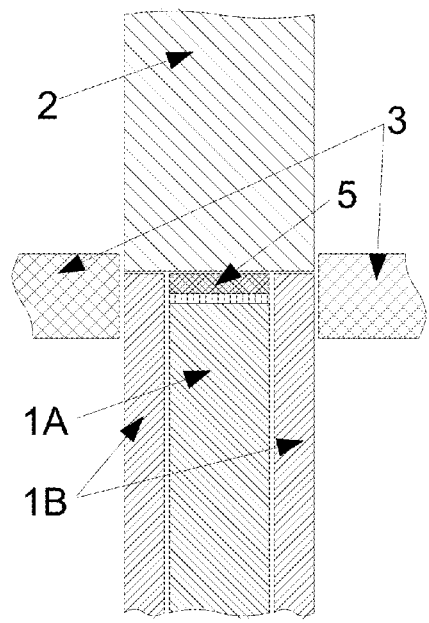
FIG. 11 depicts a lower punch (1A inner punch, 1B outer punch), an upper punch (2), a die (3) and shell and core material (5) in a setting with the second pressing step of an embodiment.
Figure 12:
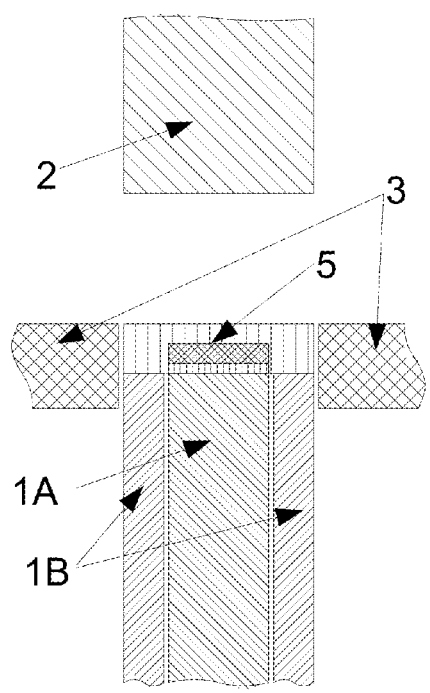
FIG. 12 depicts a lower punch (1A inner punch, 1B outer punch), an upper punch (2), a die (3), and shell and core material (5) in a setting with the third filling step of an embodiment.
Figure 13:
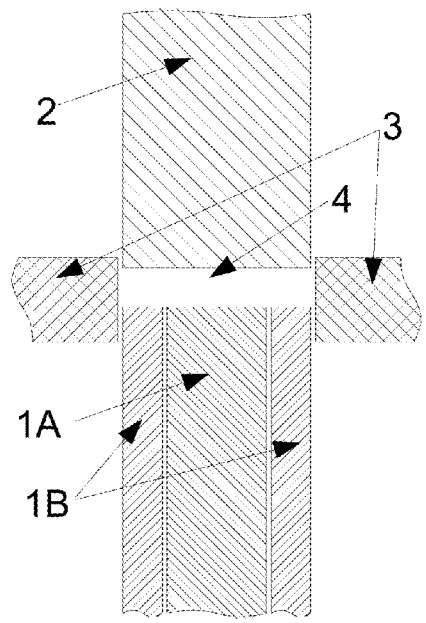
FIG. 13 depicts a lower punch (1A inner punch, 1B outer punch), an upper punch (2), a die (3) and a filling space (4) in a setting with the third pressing step of an embodiment.
Figure 14:
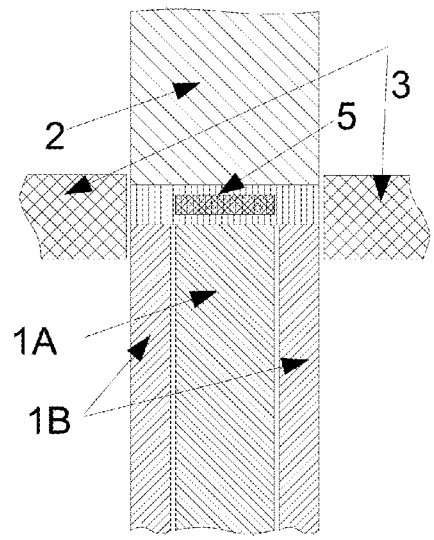
FIG. 14 depicts a lower punch (1A inner punch, 1B outer punch), an upper punch (2), a die (3) and shell and core material (5) in a setting with the third pressing step of an embodiment.
Figure 15:
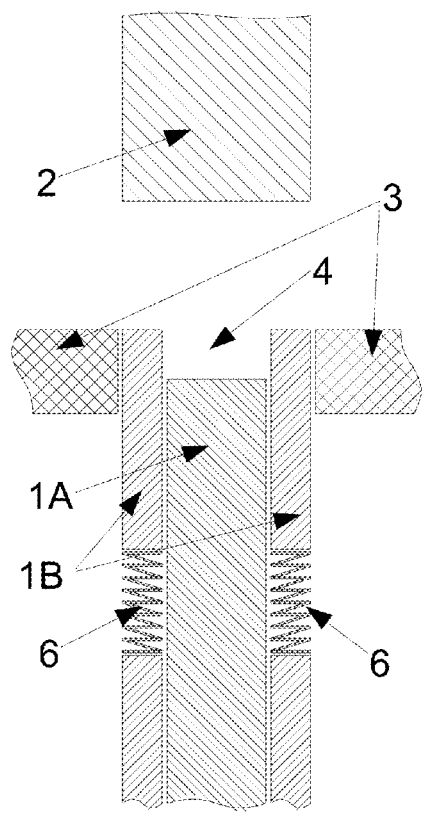
FIG. 15 depicts the same as FIG. 2, but with spring suspension (6) integrated into the outer punch.
Figure 16:
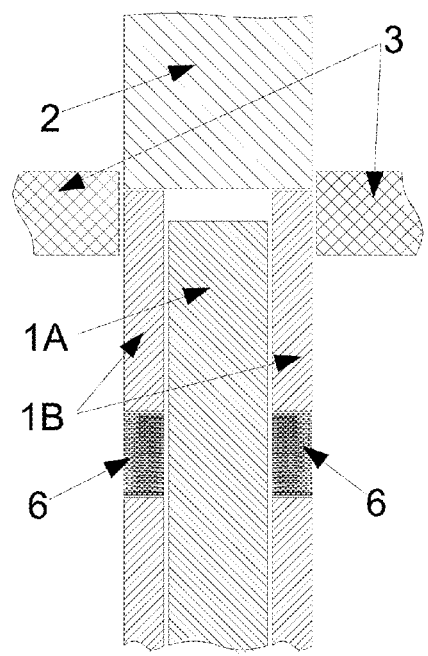
FIG. 16 depicts the same as FIG. 9, but with spring suspension (6) integrated into the outer punch.
Figure 17:
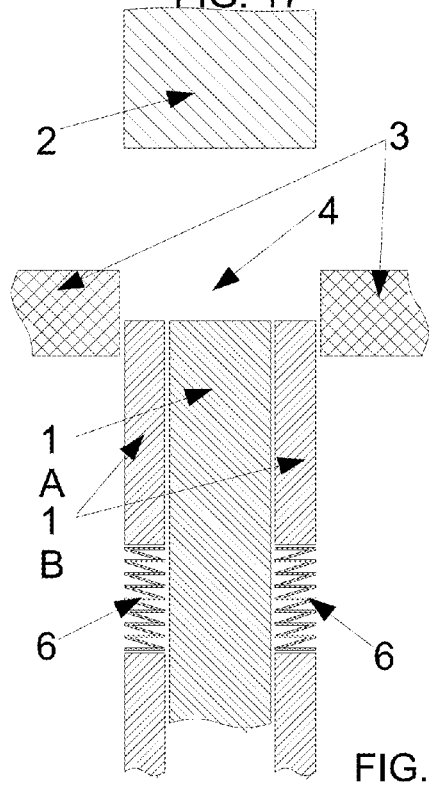
FIG. 17 depicts the same as FIG. 3, but with spring suspension (6) integrated into the outer punch.
Figure 18:
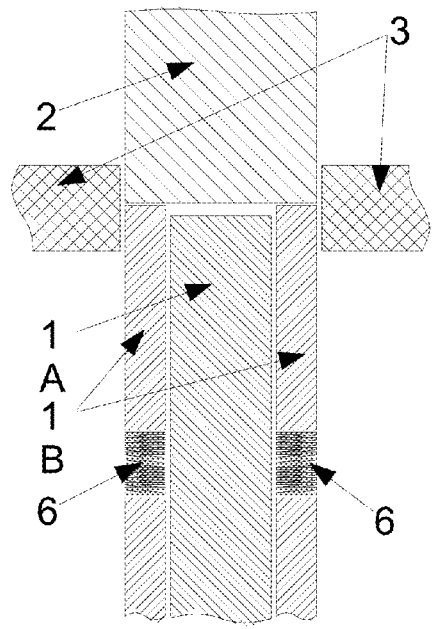
FIG. 18 depicts the same as FIG. 5, but with spring suspension (6) integrated into the outer punch.
Figure 19:
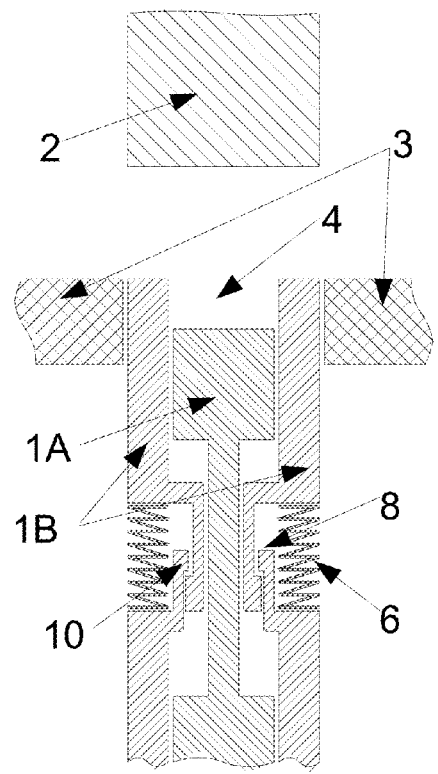
FIG. 19 depicts the same as FIG. 15, but with a limit stop (8) and a limit stop (10).
Figure 20:
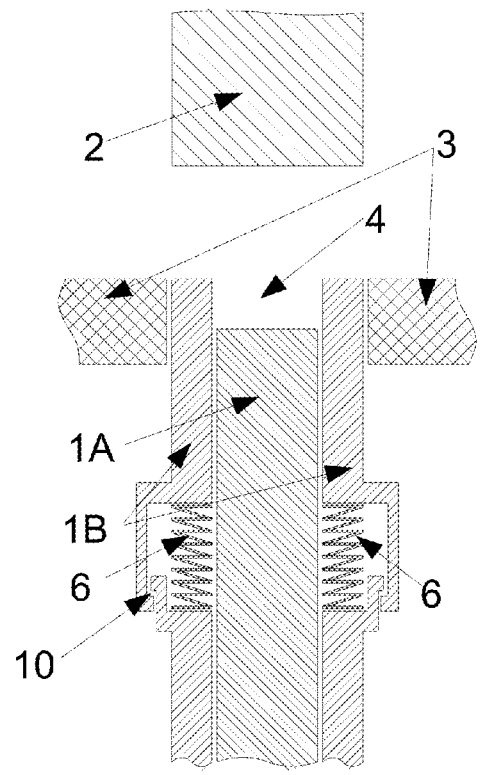
FIG. 20 depicts the same as FIG. 15, but with a limit stop (10).
Figure 21:
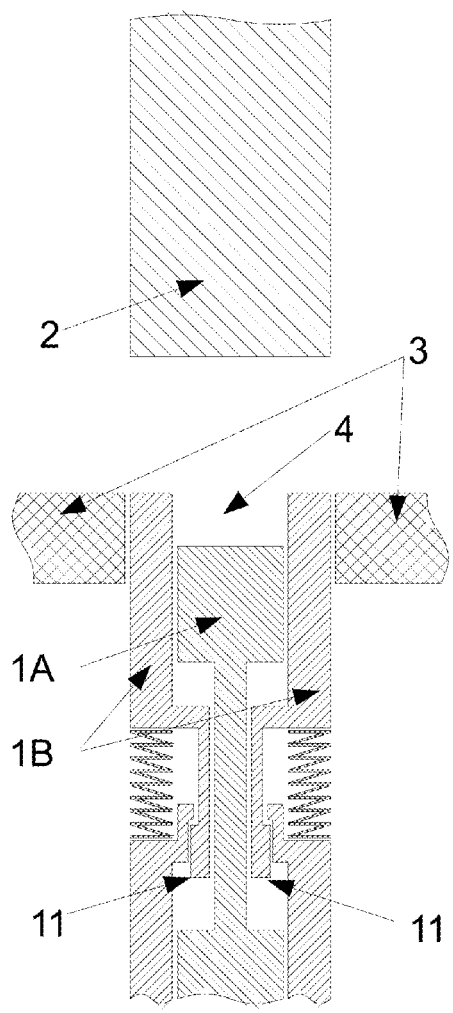
FIG. 21 depicts the same as FIG. 15, but with a limit stop (11).
Figure 22:
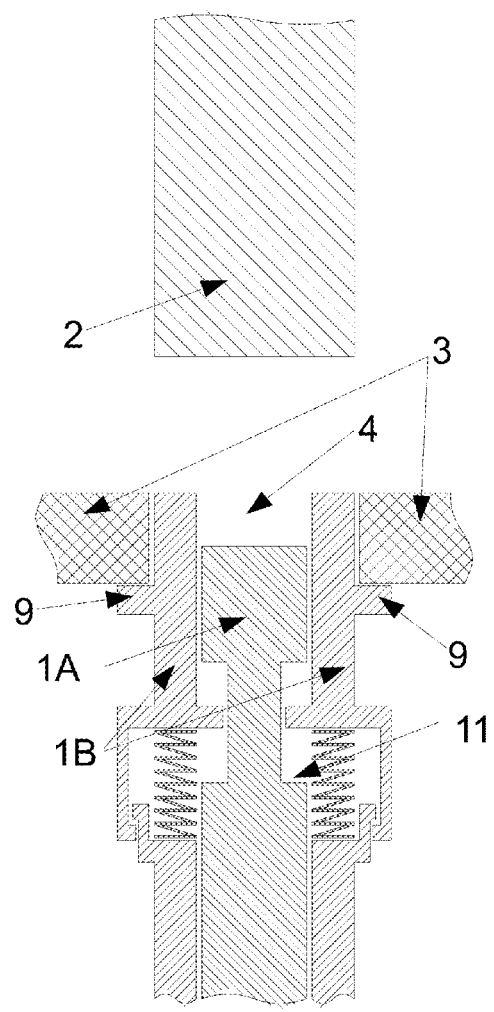
FIG. 22 depicts the same as FIG. 20, but with a limit stop (11) and a limit stop (9).
Figure 25:
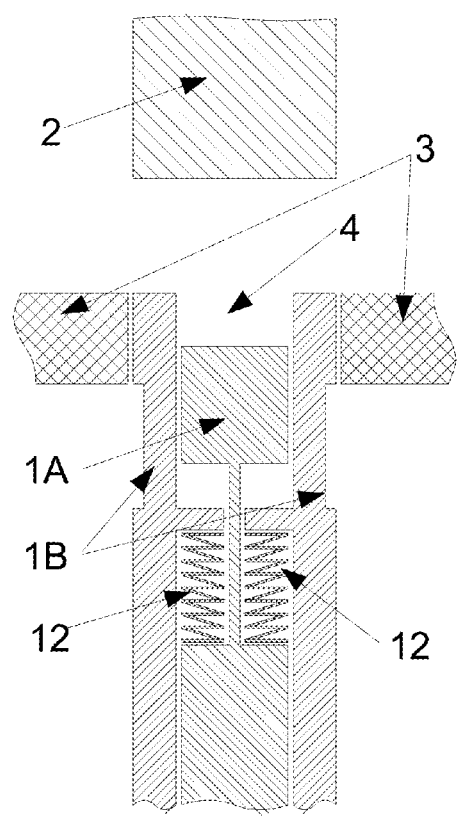
FIG. 25 depicts the same as FIG. 15, but with the spring suspension (12) of the outer punch being mounted with respect to the inner punch.
Figure 26:
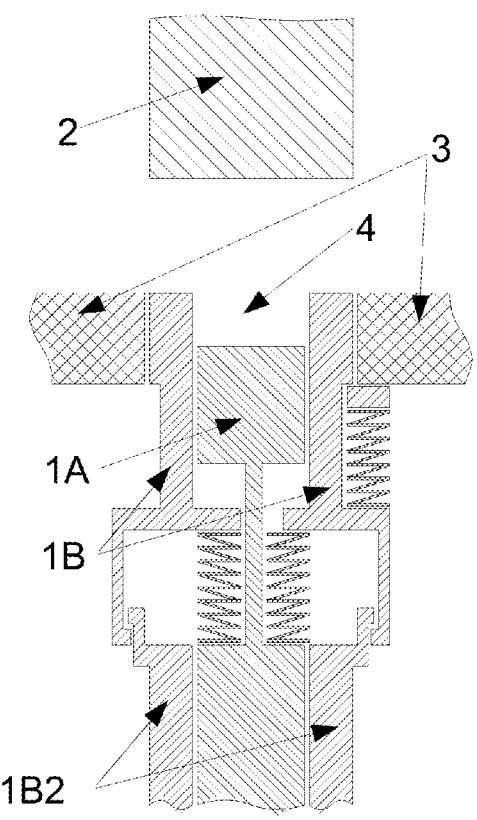
FIG. 26 depicts the same as FIG. 24, but with the spring suspension of the outer punch being mounted with respect to the inner punch.
Figure 29:
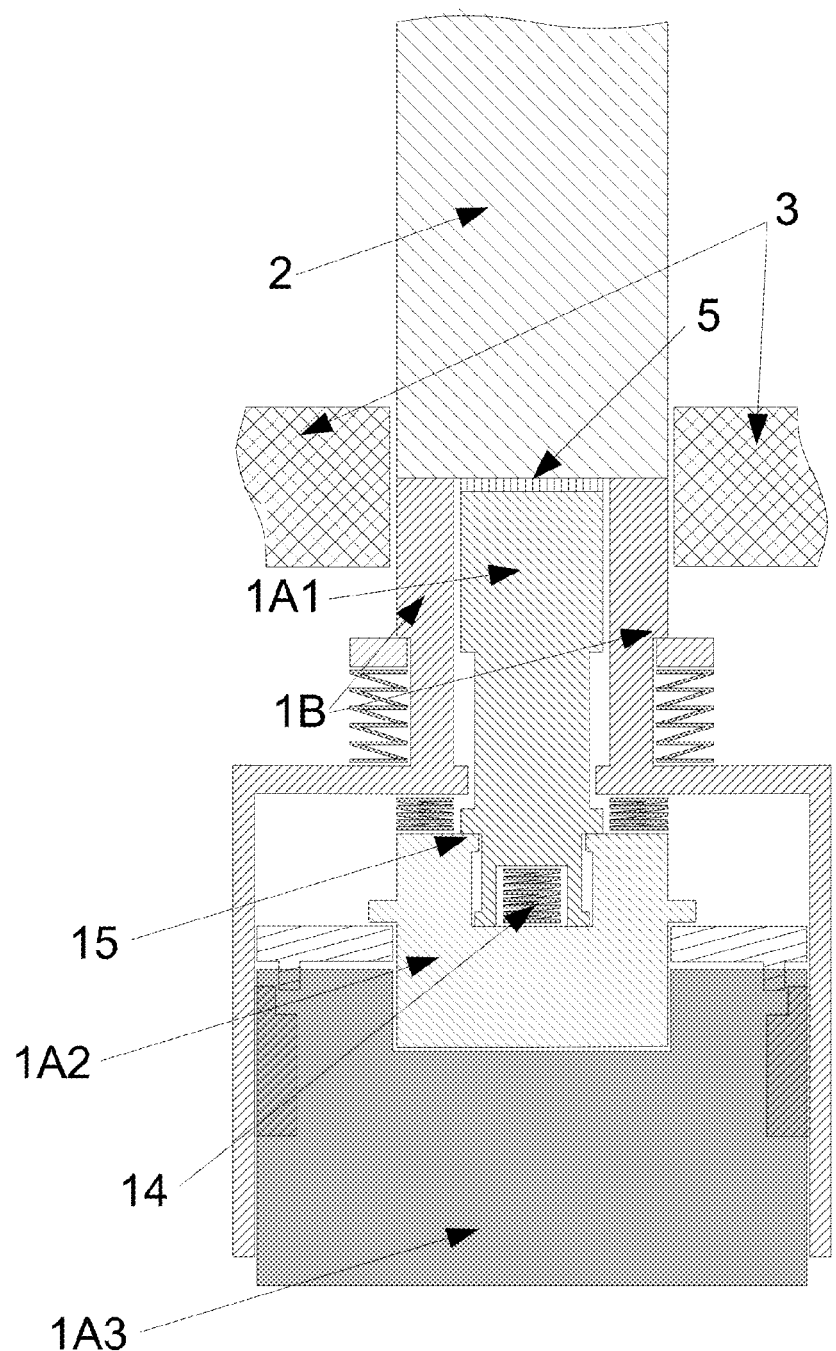
FIG. 29 depicts the same parts as FIG. 28 but with an upper punch (2) shown and the push-push mechanism in a different position
Figure 36:
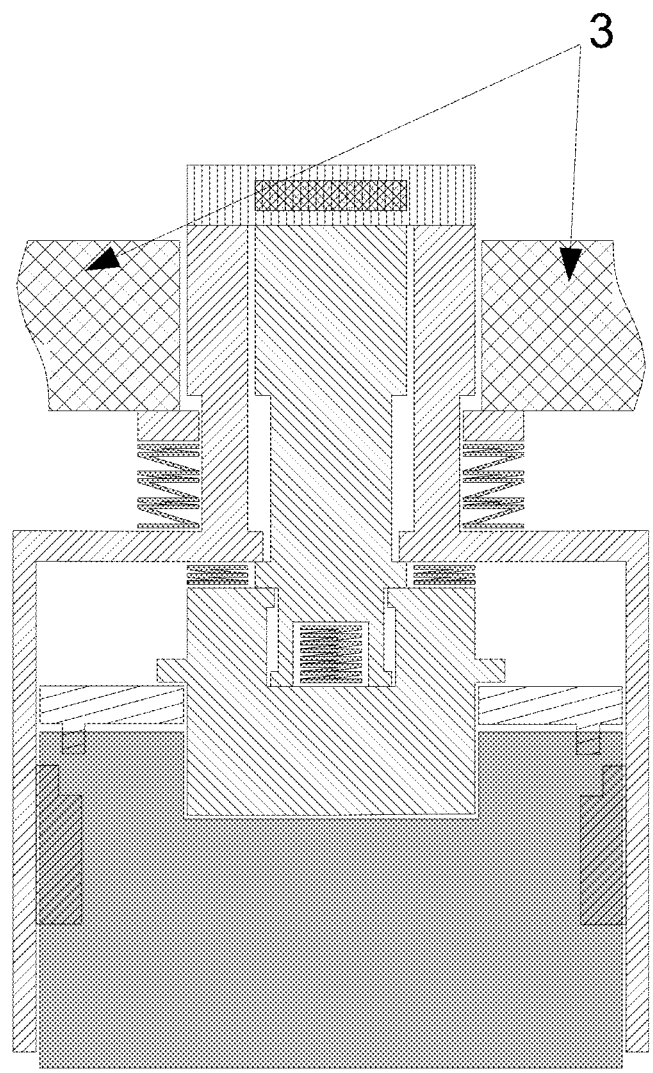
FIG. 36 depicts the same parts as FIG. 34 but in a different setting.
Figure 40:
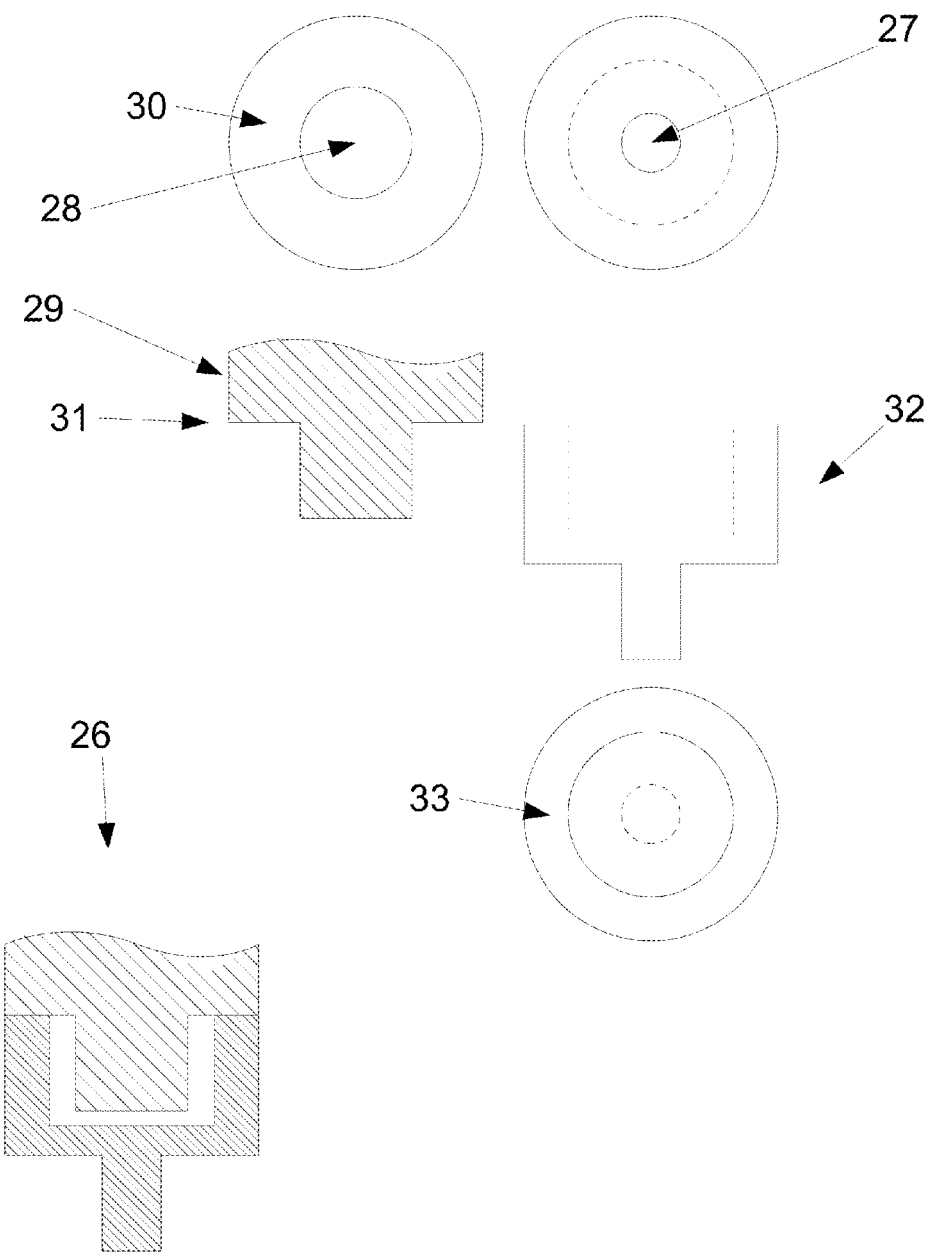
FIG. 40 depicts detail views of an upper punch (left side) and an intermediate punch (right side) and a view of both together (lower side).
Figure 41:
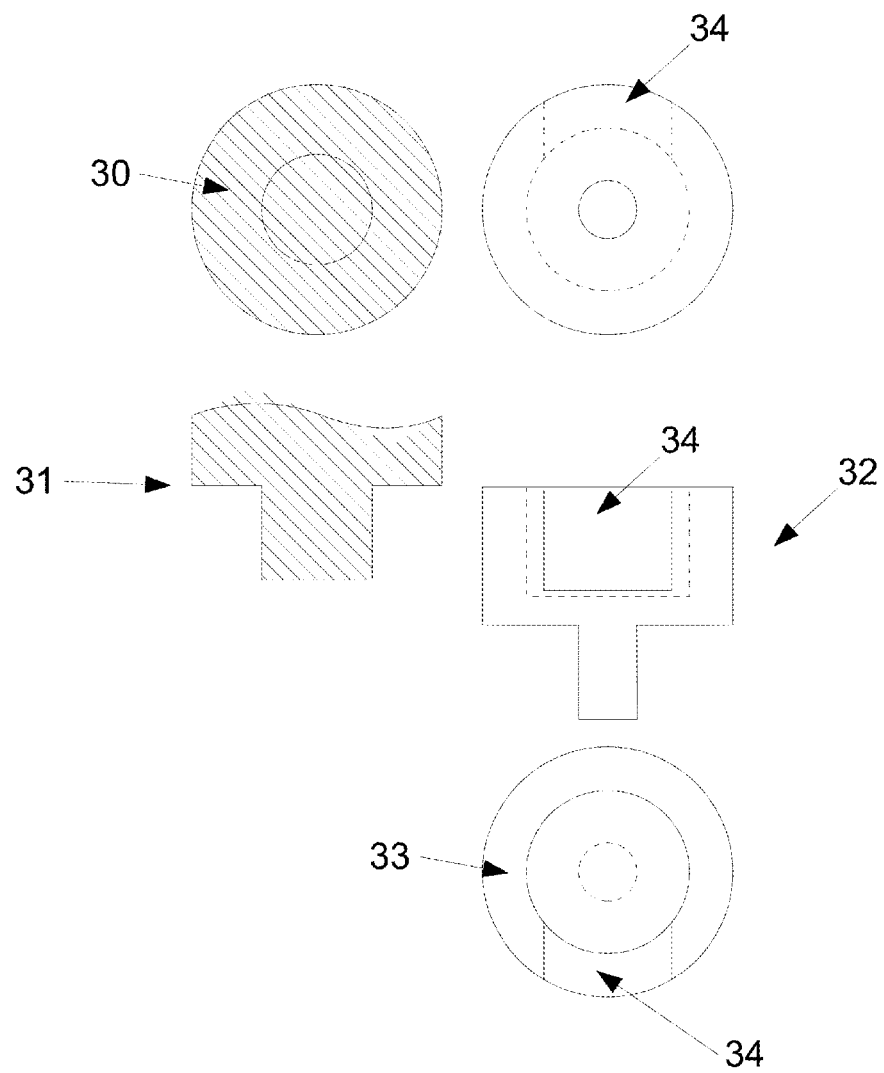
FIG. 41 depicts detail views of an upper punch (left side) and an intermediate punch (right side) with a slot.
Figure 42:
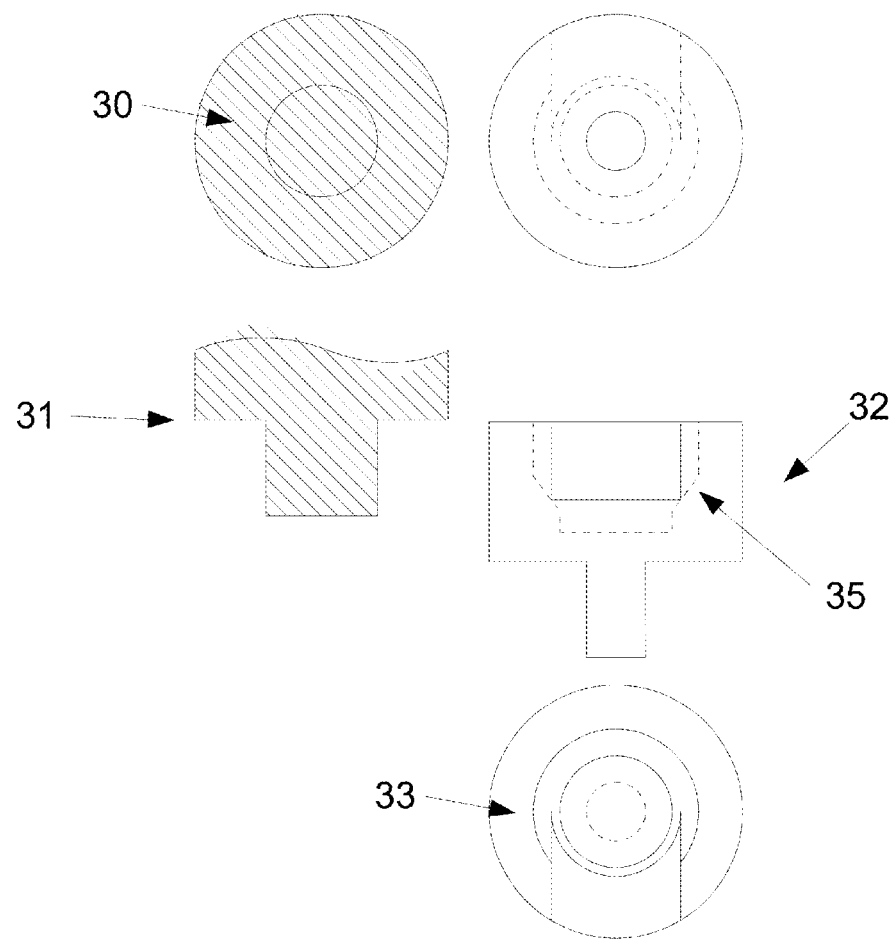
FIG. 42 depicts detail views of an upper punch (left side) and an intermediate punch (right side) with a different slot.
Figure 43:
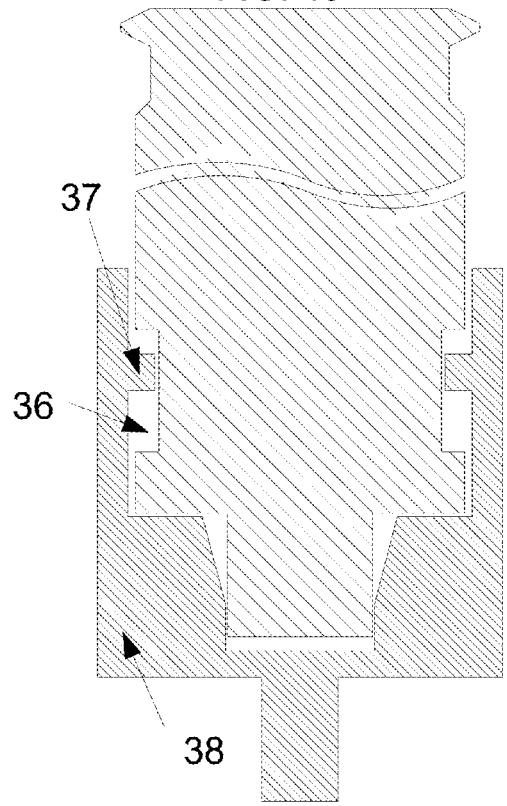
FIG. 43 depicts a cut-view of an upper punch with an intermediate punch.
Figure 44:
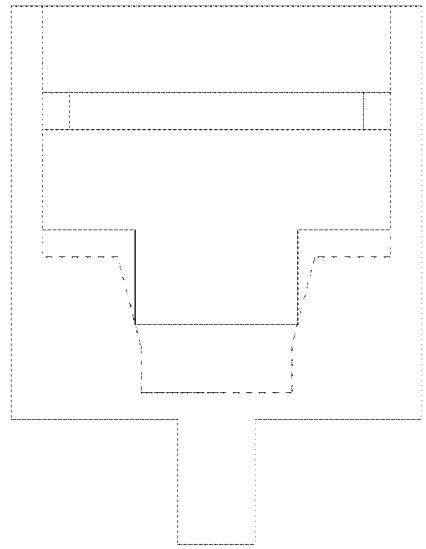
FIG. 44 depicts an intermediate punch.
Figure 45:
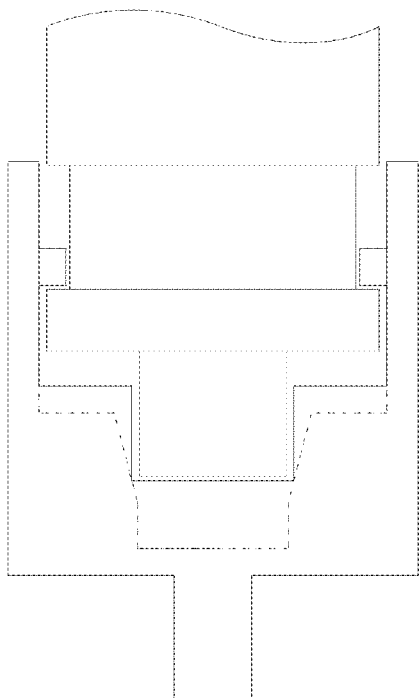
FIG. 45 depicts an upper punch with an intermediate punch.
Figure 46:
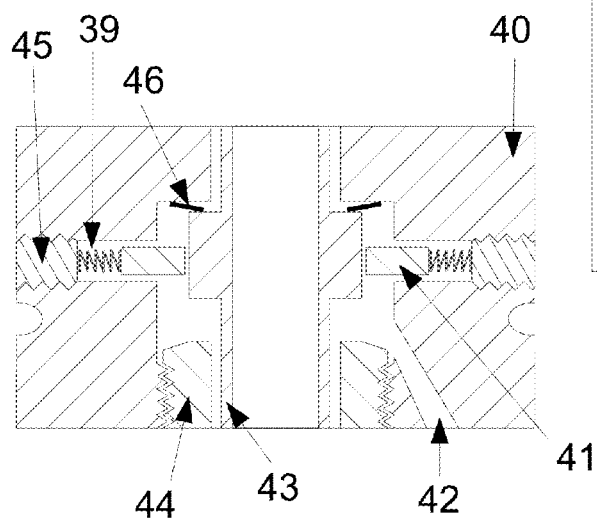
FIG. 46 depicts a die insert with a disc-shaped body (40), a tubular insert (43), a closing disc (44), brake elements (41), spring elements (39), one or more closing pieces (45), a spring suspension (46), and a further bore (42).
Figure 47:
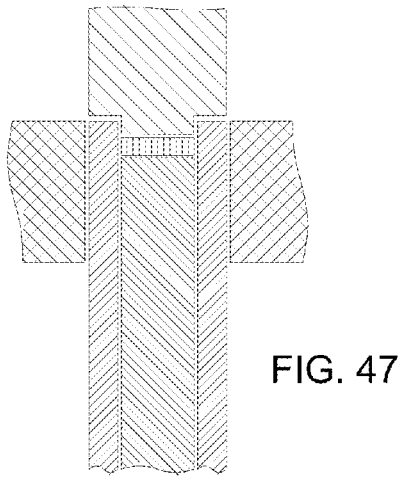
FIGS. 47 to 53 depict a die, punches and fill-in materials with various steps of a method for the production of a molding.
Figure 48:
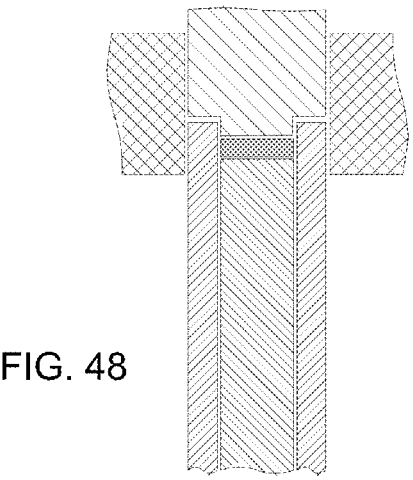
Figure 49:
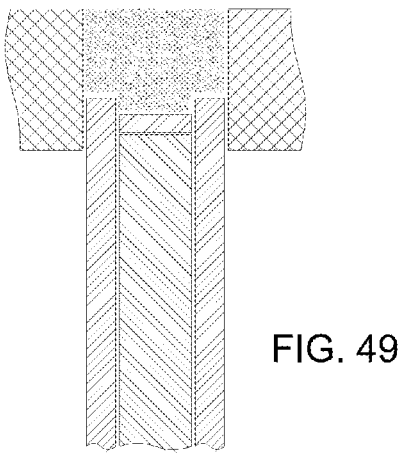
Figure 50:
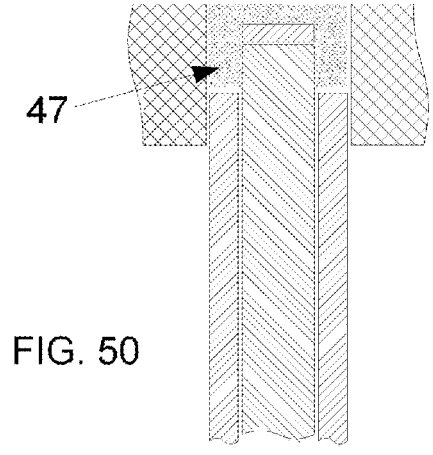
Figure 51:
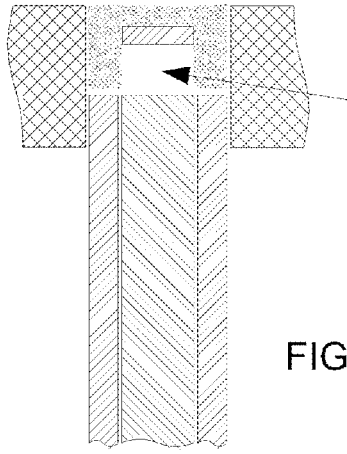
Figure 52:
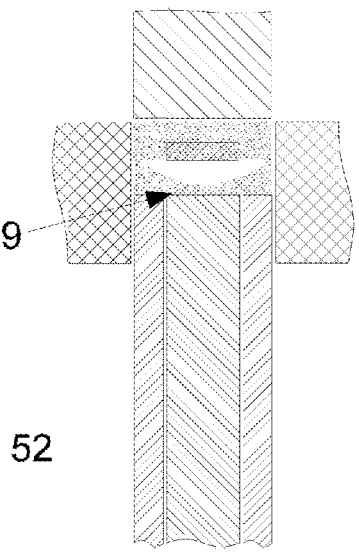
Figure 53:
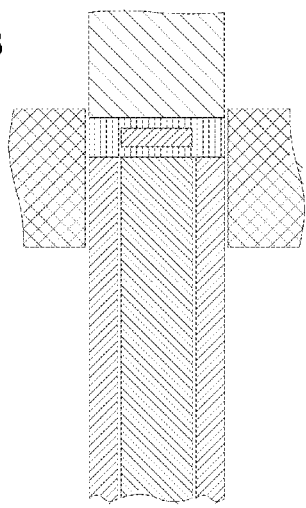
Figure 54:
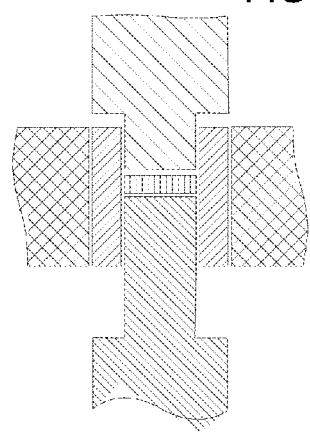
FIGS. 54 to 60 depict a die, punches, a tubular insert and fill-in materials with various steps of a method for the production of a molding.
Figure 55:
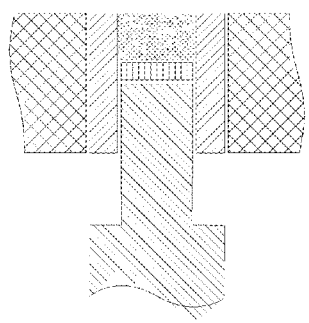
Figure 56:
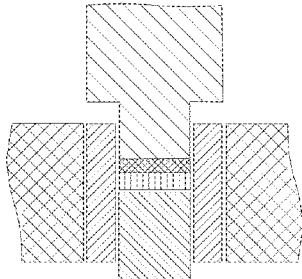
Figure 57:
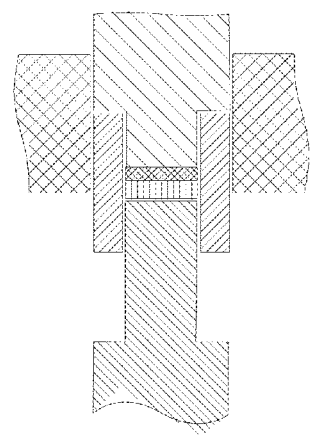
Figure 58:
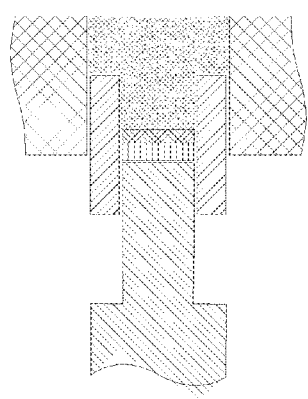
Figure 59:
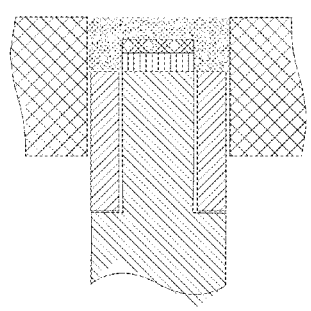
Figure 60:
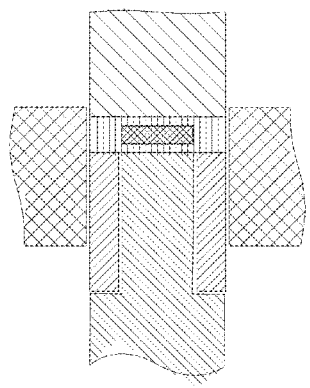
Figure 61:
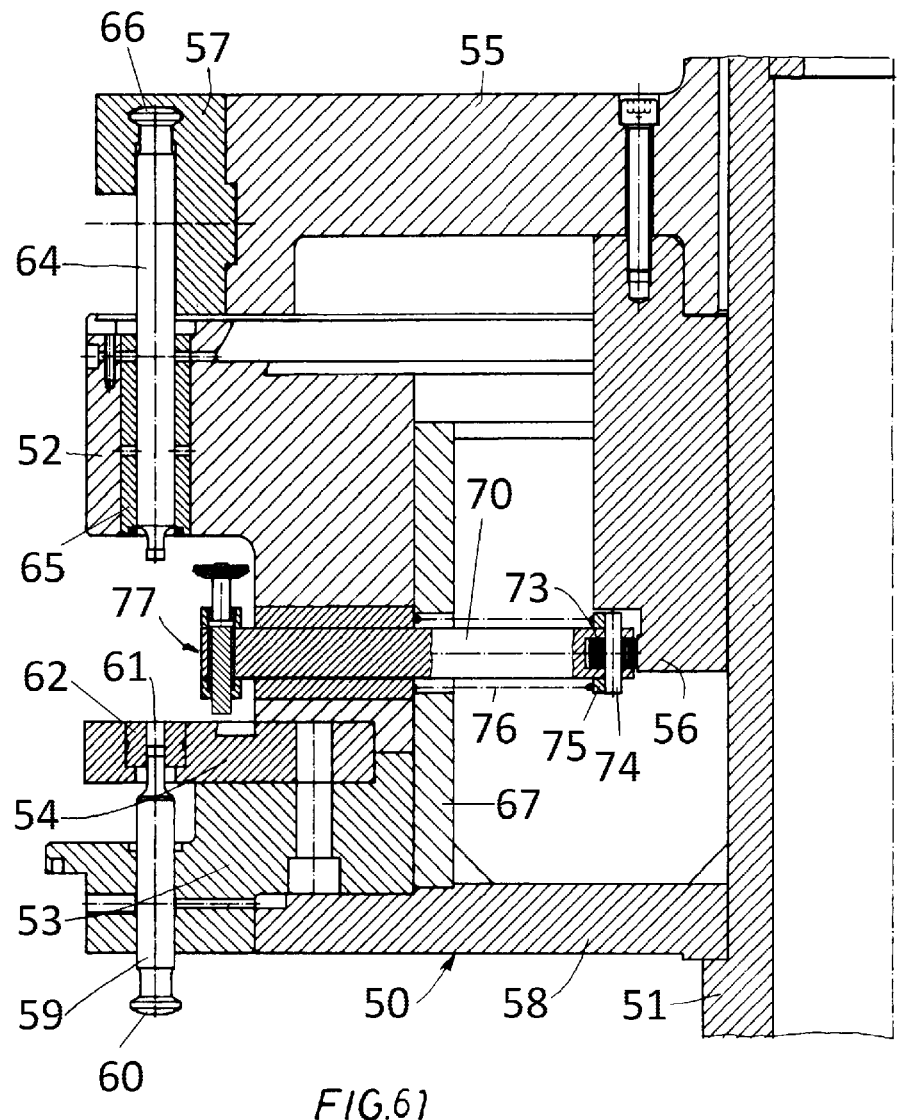
FIG. 61 depicts a vertical section through a compression molding apparatus for producing core moldings when the intermediate punch is retracted.
Figure 62:
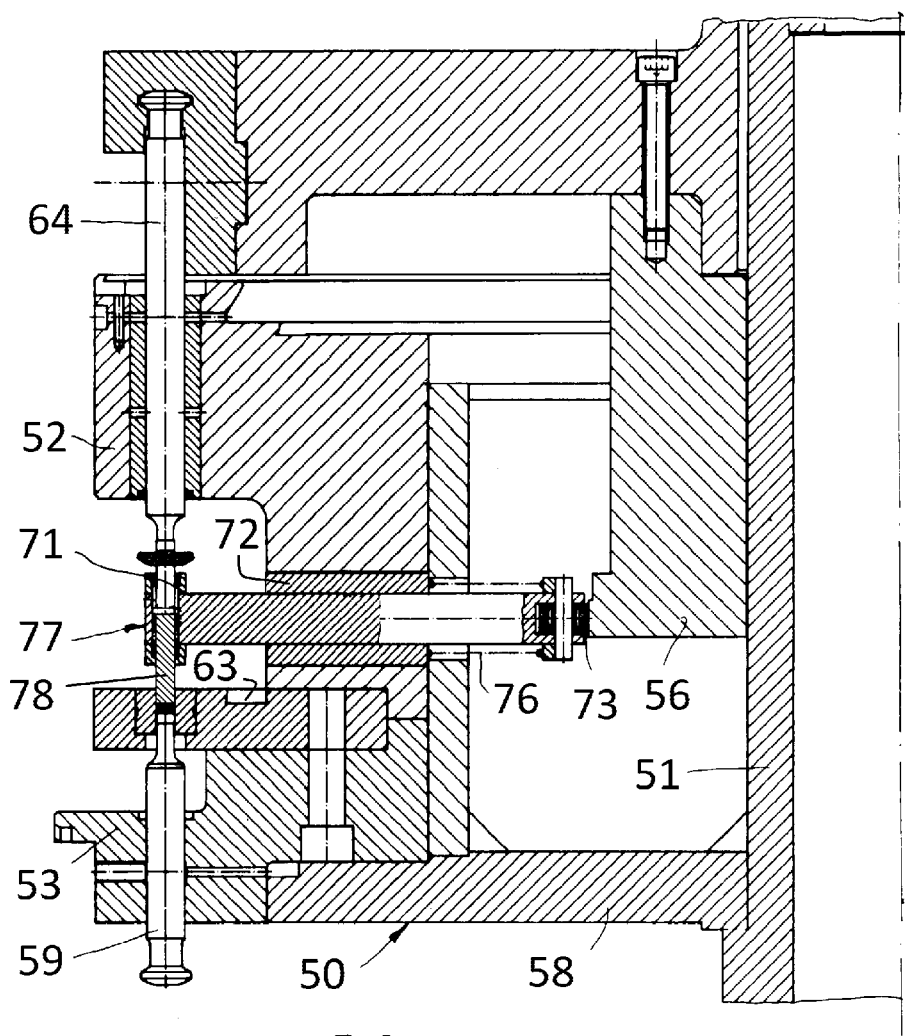
FIG. 62 depicts a vertical section through the compression molding apparatus for producing core moldings with an intermediate punch arranged below the upper punch and pressed downwards by it.
Figure 63:
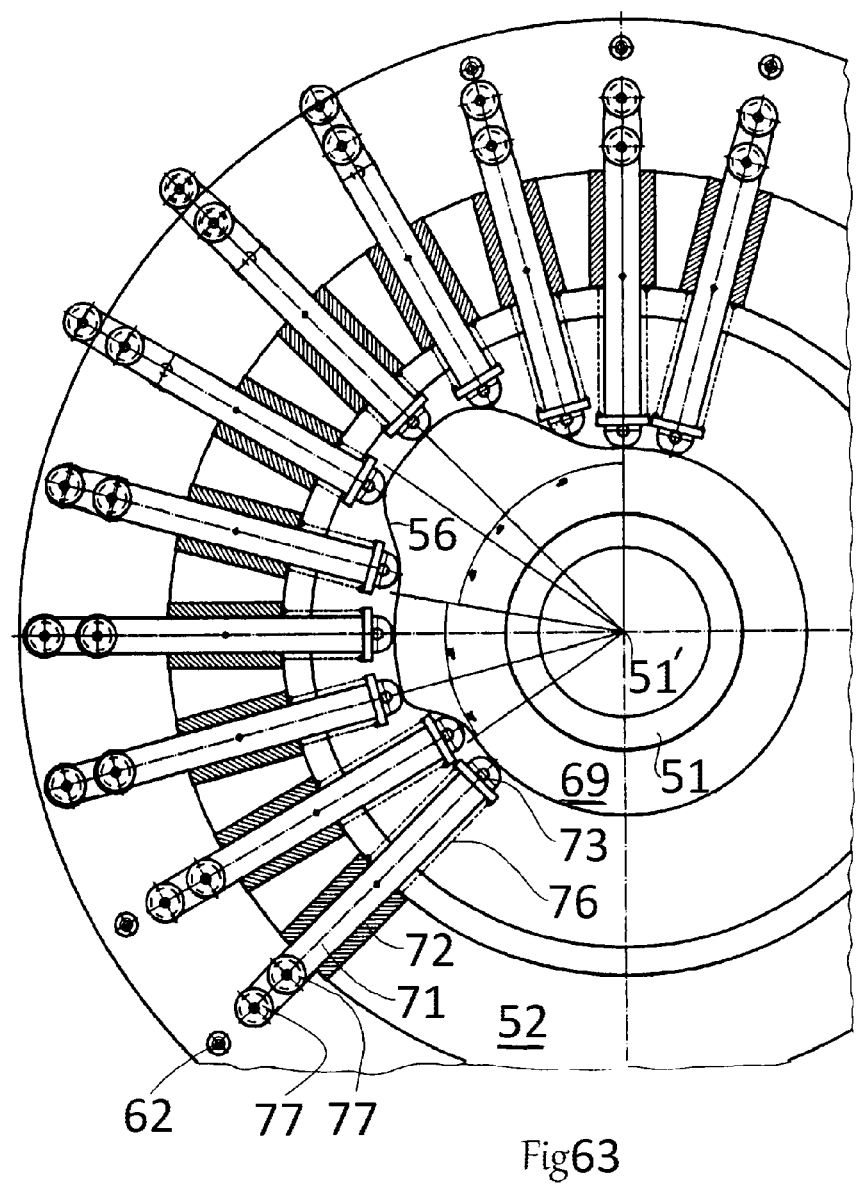
FIG. 63 depicts a principal horizontal cross section through the press with an embodiment with two intermediate punches and their holders, each.
Figure 64:
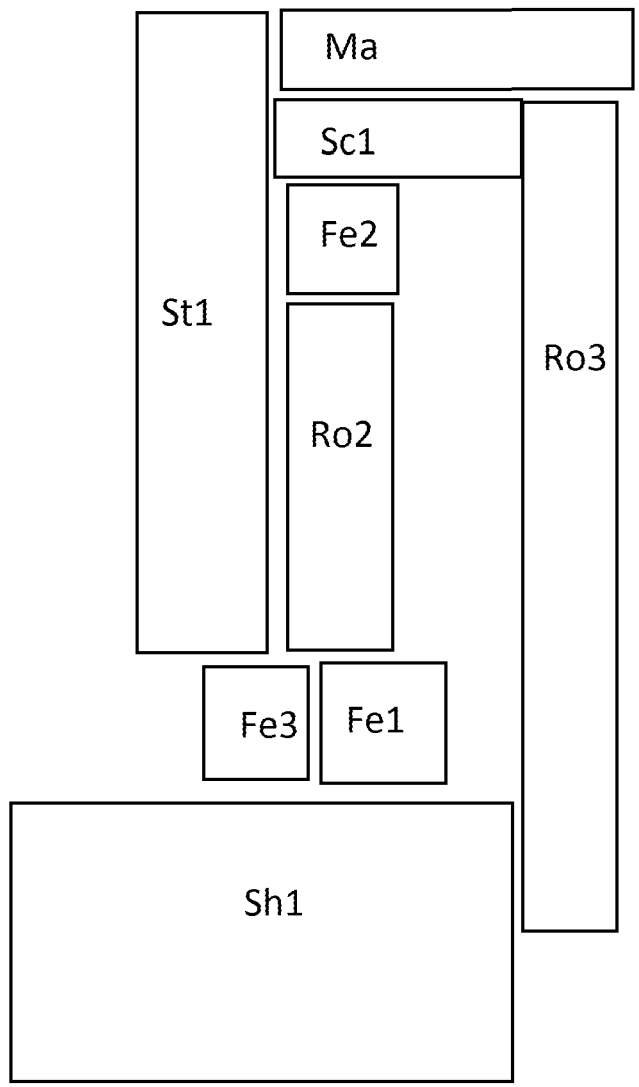
FIG. 64 depicts an embodiment of lock-in mechanisms with an outermost punch (St1), a tube (Ro2), a die (Ma), a spring (Fe1), a pretense spring (Fe2), a further disc (Sc1), a further tube Ro3, a punch shaft (Sh1), an outermost punch St1 and a further spring (Fe3).

The invention claimed is:

1. A method for the production of a molding with a core using a compression molding apparatus comprising an upper punch and a lower punch which are arranged in the vertical direction of a die, characterized
    in that the method comprises at least one step comprising positioning intermediate punch between the upper punch and the die and/or at least one step comprising removing said intermediate punch from this position, wherein the intermediate punch has a pressing surface on its underside.

2. A method according to claim 1, characterized in that the material, which the core consists of, is inserted into the die before it comes into contact with the intermediate punch, and/or
    the core material, when inserted into the die, consists of at least two particles which are not firmly connected to each other, for example, of powders, of granules, several crystals or micro-pellets,
    and/or
    the intermediate punch neither has a holdfast for the core material, nor transfers the core material from a holdfast into the die.

3. A method according to claim 1, characterized in that only the lower punch has an at least two-part structure, comprising an inner punch and an outer punch, the outer punch surrounding the outer periphery of the inner punch, wherein both the inner punch and the outer punch can perform both shifting movements and compression steps.

4. A method according to claim 1, characterized in that the sequence of the method comprises:
   A supply step 1 of an outer layer, with which molding material for a first part of the outer layer is supplied into a recess above the lower inner punch, which is enclosed by the lower outer punch;
   a core supply step, in which the molding material for the core is supplied into a recess above the molding material for the first part of the outer layer, which has been supplied in the preceding step, and enclosed by the lower outer punch;
   a pressing step of the outer layer and the core, in which the molding material for the first part of the outer layer and the molding material for the core supplied in the preceding steps, are compression-molded;
   a supply step 2 of the outer layer, in which a molding material for a second part of the outer layer is supplied into a recess of a die above and/or around the first outer layer and the core, which have been formed in the preceding step,
   a complete pressing step, in which the first part of the outer layer, the core and the molding material for the second part of the outer layer, which has been supplied in the previous step are compression-molded; and
   a step of removing the compression-molded molding, which is carried out after the complete pressing step,
and wherein at least during one pressing step, said intermediate punch is positioned between the upper punch and the die.

5. A method according to claim 4, characterized in that it comprises, between the supplying step 1 and the core supply step, at least one pressing step of the outer layer, in which the molding material for the first part of the outer layer is compression-molded.

6. A method according to claim 1, characterized in that the sequence of the method comprises:
   a supply step 1 of an outer layer, with which molding material for a first part of the outer layer is supplied into a recess above the lower punch;
   a pressing step of the outer layer, with which a trough-shaped recess is compression-molded into the first part of the outer layer;
   a core supply step with which the molding material for the core is supplied into the trough-shaped recess of the first part of the outer layer;
   a supply step 2 of the outer layer, with which molding material for a second part of the outer layer is supplied into the die above the first part of the outer layer and the core,
   a whole complete pressing step, with which the first part of the outer layer, the core and the molding material for the second part of the outer layer, which has been supplied in the previous step, are compression-molded; and
   a step of removing the compression-molded molding, which is carried out after the complete pressing step,
and wherein at least with one pressing step, said intermediate punch is positioned between the upper punch and the die.

7. A method according to claim 6, characterized in that a pressing step of the outer layer and the core, with which at least the molding material for the core supplied with the preceding step is pressed, is inserted between the core supply step and the supply step 2 of the outer layer.

8. A method according to claim 1, characterized in that only
   the lower punch has a three-part structure consisting of an inner punch, an outer punch and an outermost punch, the outer punch surrounding the outer edge of the inner punch and the outermost punch surrounding the outer edge of the outer punch, wherein the inner punch, the outer punch and the outermost punch can perform both shifting movements and compression steps.

9. A method according to claim 8, characterized in that the sequence of the method comprises:
   a supply step 1 of an outer layer, with which the molding material for a first part of the outer layer is supplied in a recess above the lower inner punch, which is enclosed by the lower outer punch;
   a core supply step, in which the molding material for the core is supplied into a recess above the molding material for the first part of the outer layer, which has been supplied in the previous step, and enclosed by the lower outer punch;
   a pressing step of the outer layer and the core, in which the molding material for the first part of the outer layer and the molding material for the core supplied in the preceding steps, are compression-molded;
   a supply step 2 of the outer layer, in which a molding material for a second part of the outer layer is supplied into a recess above and if applicable laterally of the molding material, which has been supplied in the preceding steps, enclosed by the lower outermost punch;
   a pressing step in which the first outer layer, the core and the molding material for the second outer layer, which have been supplied in the preceding step are compression-molded;
   a supply-step 3 of an outermost layer, in which a molding material for the outermost layer is supplied into a recess above and if applicable laterally of the molding material that has been supplied and pressed in the preceding steps;
   a lowering step in which the lower inner punch and the lower outer punch are lowered;
   a complete pressing step, in which the outermost layer, the outer layer and the core material are compression-molded; and
   a step of removing the compression-molded molding, which is carried out after the complete pressing step,
and
wherein at least with one pressing step, said intermediate punch is positioned between the upper punch and the die.

10. A method according to claim 4, characterized in that with the pressing steps of the first part of the outer layer and the core the intermediate punch is moved downwards by the upper punch.

11. A method according to claim 1, characterized in that the upper punch moves in a circular path around an axis and that the intermediate punch is positioned between the upper punch and the die over a partial circle of the circular path of the upper punch.

12. A method according to claim 1, characterized in that one or more intermediate punches are mounted in a fixture that is arranged rotatable around an axis which is parallel to a main axis of the molding apparatus.

13. A method according to claim 1, characterized in that the compression molding apparatus comprises a die table, an upper punch guide, a lower punch guide and a mounting of the intermediate punch and that the mounting of the intermediate punch is fixed to the die table, the upper punch guide, the lower punch guide or a part of the compression molding apparatus which is moving synchronously with those.

14. A method according to claim 1, characterized in that the compression molding apparatus comprises a die or a die insert with a tubular insert, the tubular insert being vertically shiftable with respect to the die or the die insert.

15. A method according to claim 14, characterized in that the vertical movement of the tubular insert with respect to the die or the die insert is limited by one or more limit stops and/or by requiring a certain minimum force upon it in order to be moved.

16. A compression molding apparatus comprising an upper punch and a lower punch which are arranged in the vertical direction of a die, characterized in that the compression molding apparatus comprises an intermediate punch, and a device with which the intermediate punch can be positioned between the upper punch and the die, wherein the intermediate punch has a pressing surface on its underside.

17. A compression molding apparatus according to claim 16, characterized in that the intermediate punch can be removed from the position between the upper punch and the die by using a device.

18. A compression molding apparatus according to claim 16, characterized in that the intermediate punch has no holdfast at its underside.

19. A compression molding apparatus according to claim 16, characterized in that the compression molding apparatus comprises a die or a die insert with a tubular insert, the tubular insert being vertically shiftable with respect to the die or the die insert.

20. A compression molding apparatus according to claim 19, characterized in that the vertical movement of the tubular insert with respect to the die or the die insert is limited by one or more limit stops and/or by requiring a certain minimum force upon it in order to be moved.

* * * * *